(12) United States Patent
Mwikirize et al.

(10) Patent No.: US 11,638,569 B2
(45) Date of Patent: May 2, 2023

(54) COMPUTER VISION SYSTEMS AND METHODS FOR REAL-TIME NEEDLE DETECTION, ENHANCEMENT AND LOCALIZATION IN ULTRASOUND

(71) Applicant: Rutgers, The State University of New Jersey, New Brunswick, NJ (US)

(72) Inventors: Cosmas Mwikirize, Wakiso (UG); John L. Nosher, Basking Ridge, NJ (US); Ilker Hacihaliloglu, Piscataway, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 16/436,284

(22) Filed: Jun. 10, 2019

(65) Prior Publication Data

US 2019/0378293 A1 Dec. 12, 2019

Related U.S. Application Data

(60) Provisional application No. 62/682,456, filed on Jun. 8, 2018.

(51) Int. Cl.
*G06T 7/70* (2017.01)
*G06T 5/00* (2006.01)
(Continued)

(52) U.S. Cl.
CPC .............. *G06T 7/70* (2017.01); *A61B 5/725* (2013.01); *A61B 5/7267* (2013.01);
(Continued)

(58) Field of Classification Search
CPC .. G06T 7/70; G06T 5/002; G06T 5/20; G06N 3/08; G06K 9/3233; A61B 8/0841; A61B 5/725; A61B 8/5253; A61B 5/7267
See application file for complete search history.

(56) References Cited

U.S. PATENT DOCUMENTS

| 8,357,094 B2 | 1/2013 | Mo et al. |
| 9,226,729 B2 | 1/2016 | Tashiro et al. |
| (Continued) | | |

FOREIGN PATENT DOCUMENTS

| CN | 103886617 A | 6/2014 |
| CN | 104248454 B | 6/2016 |
| EP | 2735271 A1 | 5/2014 |

OTHER PUBLICATIONS

Korbe, et al., "Ultrasound-Guided Interventional Procedures for Chronic Pain Management," Pain Management, 5(6), pp. 466-482 (2015) (18 pages).

(Continued)

*Primary Examiner* — Kevin Ky
(74) *Attorney, Agent, or Firm* — McCarter & English, LLP

(57) ABSTRACT

Systems and methods for detecting placement of an object in a digital image are provided. The system receives a digital image and processes the digital image to generate one or more candidate regions within the digital image using a first neural network. The system then selects a proposed region from the one or more candidate regions using the first neural network and assigns a score to the proposed region using the first neural network. Lastly, the system processes the proposed region using a second neural network to detect an object in the proposed region.

22 Claims, 35 Drawing Sheets

(51) Int. Cl.
G06T 5/20 (2006.01)
G06V 10/25 (2022.01)
G06N 3/08 (2023.01)
A61B 8/08 (2006.01)
A61B 5/00 (2006.01)

(52) U.S. Cl.
CPC .......... *A61B 8/0841* (2013.01); *A61B 8/5253* (2013.01); *G06N 3/08* (2013.01); *G06T 5/002* (2013.01); *G06T 5/20* (2013.01); *G06V 10/25* (2022.01); *G06T 2207/10132* (2013.01); *G06T 2207/20084* (2013.01); *G06T 2207/30241* (2013.01)

(56) References Cited

U.S. PATENT DOCUMENTS

| | | | |
|---|---|---|---|
| 9,364,294 | B2 | 6/2016 | Razzaque et al. |
| 9,398,936 | B2 | 7/2016 | Razzaque et al. |
| 9,561,019 | B2 | 2/2017 | Mihailescu et al. |
| 9,792,686 | B2 | 10/2017 | Zalev |
| 9,858,496 | B2 | 1/2018 | Sun et al. |
| 9,881,234 | B2 | 1/2018 | Huang et al. |
| 10,013,773 | B1* | 7/2018 | Ogale ................ G06V 10/764 |
| 10,206,655 | B2 | 2/2019 | Woo et al. |
| 10,213,110 | B2 | 2/2019 | Wang et al. |
| 10,232,194 | B2 | 3/2019 | Schlosser et al. |
| 2003/0189980 | A1 | 10/2003 | Dvir et al. |
| 2004/0049109 | A1 | 3/2004 | Thornton |
| 2006/0171594 | A1 | 8/2006 | Avidan et al. |
| 2007/0167801 | A1 | 7/2007 | Webler et al. |
| 2008/0146932 | A1* | 6/2008 | Chalana ................ A61B 8/0866 600/447 |
| 2012/0046971 | A1* | 2/2012 | Walker .................. A61B 6/488 382/128 |
| 2013/0077442 | A1 | 3/2013 | Hersey |
| 2014/0140597 | A1 | 5/2014 | Barzelay et al. |
| 2015/0209599 | A1 | 7/2015 | Schlosser et al. |
| 2015/0256761 | A1 | 9/2015 | Umezawa |
| 2015/0320374 | A1 | 11/2015 | Uehara et al. |
| 2015/0346303 | A1 | 12/2015 | Hu et al. |
| 2016/0048737 | A1 | 2/2016 | Kam et al. |
| 2016/0155227 | A1 | 6/2016 | Chae |
| 2016/0213430 | A1* | 7/2016 | Mucha .................. A61B 5/062 |
| 2016/0242811 | A1 | 8/2016 | Sadiq et al. |
| 2016/0317118 | A1* | 11/2016 | Parthasarathy ......... G06T 7/143 |
| 2016/0328643 | A1* | 11/2016 | Liu ...................... G06V 10/443 |
| 2017/0027701 | A1 | 2/2017 | Mahfouz |
| 2017/0143312 | A1 | 5/2017 | Hedlund et al. |
| 2017/0188990 | A1 | 7/2017 | Von Allmen et al. |
| 2017/0206431 | A1* | 7/2017 | Sun ...................... G06F 16/5838 |
| 2017/0258451 | A1 | 9/2017 | Sakanashi et al. |
| 2017/0330319 | A1* | 11/2017 | Xu ........................ A61B 5/4887 |
| 2018/0075628 | A1* | 3/2018 | Teare .................... G06K 9/6274 |
| 2018/0158209 | A1 | 6/2018 | Fine et al. |
| 2018/0161502 | A1* | 6/2018 | Nanan ....................... A61B 5/15 |
| 2018/0173971 | A1* | 6/2018 | Jia ........................ G06N 3/0454 |
| 2018/0193122 | A1* | 7/2018 | Yoshida ............. A61C 17/3418 |
| 2018/0325602 | A1 | 11/2018 | Bharat et al. |
| 2018/0333112 | A1 | 11/2018 | Weber et al. |
| 2018/0338793 | A1 | 11/2018 | Sulkin et al. |
| 2018/0368807 | A1 | 12/2018 | Van De Pas et al. |
| 2018/0368883 | A1 | 12/2018 | Rossa et al. |
| 2019/0019037 | A1* | 1/2019 | Kadav ................ G06K 9/00744 |
| 2019/0069882 | A1 | 3/2019 | Moctezuma de la Barrera et al. |
| 2019/0231441 | A1 | 8/2019 | Vaughan et al. |
| 2019/0247130 | A1 | 8/2019 | State et al. |
| 2019/0325653 | A1* | 10/2019 | Yip ...................... G06F 3/04883 |
| 2019/0336107 | A1 | 11/2019 | Hope Simpson et al. |
| 2019/0336108 | A1 | 11/2019 | Hope Simpson et al. |
| 2019/0340462 | A1* | 11/2019 | Pao ....................... G06T 3/4053 |
| 2019/0378293 | A1* | 12/2019 | Mwikirize ........... A61B 8/0841 |
| 2020/0037983 | A1 | 2/2020 | Poland |
| 2020/0076842 | A1 | 3/2020 | Zhou et al. |
| 2020/0167601 | A1* | 5/2020 | Deng ..................... G06V 20/47 |
| 2020/0311943 | A1* | 10/2020 | Dai ...................... G06K 9/6256 |
| 2020/0342305 | A1 | 10/2020 | Du et al. |
| 2021/0068791 | A1 | 3/2021 | Gebre |
| 2021/0110532 | A1 | 4/2021 | Braman et al. |

OTHER PUBLICATIONS

Karamalis, et al., "Ultrasound Confidence Maps Using Random Walks," Medical Image Analysis 16 pp. 1101-1112 (2012) (12 pages).

Osher, "The Split Bregman Method for L1-Regularized Problems," SIAM Journal on Imaging Sciences, Jan. 2009 (29 pages).

Everingham, et al., "The PASCAL Visual Object Classes (VOC) Challenge," Int J Comput Vis 88: pp. 303-338 (2010) (36 pages).

Elsharkawy, et al., "The Infiniti Plus Ultrasound Needle Guidance System Improves Needle Visualization During the Placement of Spinal Anesthesia," Korean Journal of Anesthesiology, vol. 69, No. 4, pp. 417-419, Aug. 2016 (3 pages).

Beigi, et al., "Spectral Analysis of the Tremor Motion for Needle Detection in Curvilinear Ultrasound via Spatiotemporal Linear Sampling," Int J Comput Assist Radiol Surg, 11, pp. 1183-1192 (2016) (10 pages).

Mwikirize, et al., "Signal Attenuation Maps for Needle Enhancement and Localization in 2D Ultrasound," International Journal of Computer Assisted Radiology and Surgery, 13, pp. 363-374 (2018) (12 pages).

Klambauer, et al., "Self-Normalizing Neural Networks," arXiv:1706.02515v5, Sep. 7, 2017 (102 pages).

Mathiassen, et al., "Robust Real-Time Needle Tracking in 2-D Ultrasound Images Using Statistical Filtering," IEEE Transactions on Control Systems Technology, vol. 25, No. 3, pp. 966-978, May 2017 (13 pages).

Pourtaherian, et al., "Robust and Semantic Needle Detection in 3D Ultrasound Using Orthogonal-Plane Convolutional Neural Networks," International Journal of Computer Assisted Radiology and Surgery 13, pp. 1321-1333 (2018) (13 pages).

Priester, et al., "Robotic Ultrasound Systems in Medicine," IEEE Transactions on Ultrasonics, Ferroelectrics, and Frequency Control, vol. 60, No. 3, pp. 507-523, Mar. 2013 (17 pages).

Fevre, et al., "Reduced Variability and Execution Time to Reach a Target with a Needle GPS System: Comparison Between Physicians, Residents and Nurse Anaesthetists," Anaesth Crit Care Pain Med 37, pp. 55-60 (2018) (6 pages).

Prasad, et al., "Real-Time Ultrasound-Guided Percutaneous Renal Biopsy with Needle Guide by Nephrologists Decreases Post-Biopsy Complications," Clin Kidney J, 8: pp. 151-156 (2015) (6 pages).

Clendenen, et al., "Real-Time Three-Dimensional Ultrasound-Assisted Axillary Plexus Block Defines Soft Tissue Planes," International Anesthesia Research Society, vol. 108, No. 4, pp. 1347-1350, Apr. 2009 (4 pages).

Grady, "Random Walks for Image Segmentation," IEEE Transactions on Pattern Analysis and Machine Intelligence, vol. 28, No. 11, Nov. 2006 (16 pages).

Xia, et al., "Looking Beyond the Imaging Plane: 3D Needle Tracking with a Linear Array Ultrasound Probe," Scientific Reports 7:3674 (2017) (9 pages).

Xia, et al.," In-Plane Ultrasonic Needle Tracking Using a Fiber-Optic Hydrophone," Med Phys 42, pp. 5983-5991, Oct. 2015 (16 pages).

Welleweerd, et al., "Design of an End Effector for Robot-Assisted Ultrasound-Guided Breast Biopsies," International Journal of Computer Assisted Radiology and Surgery 15, pp. 681-690 (2020) (10 pages).

Redmon, et al., "You Only Look Once: Unified, Real-Time Object Detection," arXiv:1506.02640v5, May 9, 2016 (10 pages).

Neubach, et al., "Ultrasound-Guided Robot for Flexible Needle Steering," IEEE Transactions on Biomedical Engineering, vol. 57, No. 4, pp. 799-805, Apr. 2010 (7 pages).

Huang, et al., "The Principles and Procedures of Ultrasound-Guided Anesthesia Techniques," Cureus 10(7): e2980 (2018) (8 pages).

(56) References Cited

OTHER PUBLICATIONS

Najafi, et al., "Single-Camera Closed-Form Real-Time Needle Tracking for Ultrasound-Guided Needle Insertion," Ultrasound in Med. & Biol., vol. 41, No. 10, pp. 2663-2676 (2015) (14 pages).
Mwikirize, et al., "Single Shot Needle Localization in 2D Ultrasound," MICCAI 2019, LNCS 11768, pp. 637-645 (9 pages).
Marhofer, et al., "Safe performance of Peripheral Regional Anaesthesia: The Significance of Ultrasound Guidance," Anaesthesia 72, pp. 431-434 (2017) (4 pages).
Kim, et al., "Practical Guidelines for Ultrasound-Guided Core Needle Biopsy of Soft-Tissue Lesions: Transformation from Beginner to Specialist," Korean Journal of Radiology 18(2), pp. 361-369 (2017) (9 pages).
Umbarje, et al., "Out-of-Plane Brachial Plexus Block with a Novel SonixGPS (TM) Needle Tracking System," Anaesthesia 68: pp. 433-434 (2013) (2 pages).
Gadsden, et al., "Evaluation of the eZono 4000 with eZGuide for Ultrasound-Guided Procedures," Expert Review of Medical Devices 12(3), pp. 251-261 (2015) (12 pages).
McVicar, et al., "Novice Performance of Ultrasound-Guided Nedling Skills: Effect of a Needle Guidance System," Regional Anesthesia and Pain Medicine, vol. 40, No. 2, pp. 150-153, Mar.-Apr. 2015 (4 pages).
Mwikirize, et al., "Local Phase-Based Learning for Needle Detection and Localization in 3d Ultrasound," In Computer Assisted and Robotic Endoscopy and Clinical Image-Based Procedures, Sep. 14, 2017, Springer, Cham., pp. 108-115 (8 pages).
Mwikirize, et al., "Time-Aware Deep Neural Networks for Needle Tip Localization in 2D Ultrasound," International Journal of Computer Assisted Radiology and Surgery (2021) (9 pages).
Girshick, "Fast R-CNN," arXiv:1504.08083v2, Sep. 27, 2015 (9 pages).
Krizhevsky, et al., "Imagenet Classification with Deep Convolutional Neural Networks," Advances in Neural Information Processing Systems (2012) (9 pages).
Simonyan, et al., "Very Deep Convolutional Network for Large-Scale Image Recognition," arXiv:1409.1556v6, Apr. 10, 2015 (14 pages).
Zeiler, et al. "Visualizing and Understanding Convolutional Neural Networks," arXiv:1311.2901v3, Nov. 28, 2013 (11 pages).
Krizhevsky, "Learning Multiple Layers of Features from Tiny Images," CIFAR10 dataset, Apr. 8, 2009 (60 pages).
Huynh, et al., "Digital Mammographic Tumor Classification Using Transfer Learning from Deep Convolutional Neural Networks," Journal of Medical Imaging, vol. 3(3) (2016) (6 pages).
Ameri, et al., "Development of a High Frequency Single-Element Ultrasound Needle Transducer for Anesthesia Delivery," In: Proc. SPIE Medical Imaging: Ultrasonic Imaging and Tomography, vol. 10139 (2017) (8 pages).
International Search Report of the International Searching Authority dated Oct. 29, 2019, issued in connection with International Application No. PCT/US2019/046364 (3 pages).
Written Opinion of the International Searching Authority dated Oct. 29, 2019, issued in connection with International Application No. PCT/US2019/046364 (4 pages).
Mwikirize, et al., "Learning Needle Tip Localization from Digital Subtraction in 2D Ultrasound," International Journal of Computer Assisted Radiology and Surgery, Mar. 25, 2019 (10 pages).
Dong, et al., "A Novel Method for Enhanced Needle Localization Using Ultrasound-Guidance," ISVC 2009: Advances in Visual Computing, Nov. 30, 2009, pp. 914-923 (12 pages).
Renfrew, et al., "Active Localization and Tracking of Needle and Target in Robotic Image-Guided Intervention Systems, " Auton Robots: 42(1):83-97, Jun. 12, 2017 (39 pages).
Neubach, et al., "Ultrasound-Guided Robot for Flexibile Needle Steering," IEEE Transactions on Biomedical Engineering, vol. 57, No. 4, Apr. 4, 2010 (8 pages).
Office Action dated Sep. 3, 2021, issued in connection with U.S. Appl. No. 17/268,321 (34 pages).
Huang, et al., "Imaging Artifacts of Medical Instruments in Ultrasound-Guided Interventions," American Institute of Ultrasound in Medicine 2007, vol. 26, pp. 1303-1322 (20 pages).
Wang, et al., "Active Contour Model Coupling with Backward Diffusion for Medical Image Segmentation," 6th International Conference on Biomedical Engineering and Informatics (2013) (5 pages).
Mwikirize, et al., "Convolutional Neural Networks for Real-Time Needle Detection and Localization in 2D Ultrasound," International Journal of Computer Assisted Radiology and Surgery, Mar. 6, 2018 (11 pages).
Extended European Search Report issued by the European Patent Office issued in connection with European Patent Application No. 19850544.8 (11 pages).
Notice of Allowance dated Jan. 4, 2022, issued in connection with U.S. Appl. No. 17/268,321 (10 pages).
Hacihaliloglu, et al., "Projection-Based Phase Features for Localization of a Needle Tip in 2D Curvilinear Ultrasound," Med. Image. Comput. Assist. Interv. Springer LNCS, 9349, pp. 347-354, (2015) (8 pages).
Xiang, et al., "PoseCNN: A Convolutional Neural Network for 6D Object Pose Estimation in Cluttered Scenes," arXiv: 1711.001993, May 26, 2018 (10 pages).
Qiu, et al., "Phase Grouping-Based Needle Segmentation in 3-D Trans-rectal Ultrasound-Guided Prostate Trans-Perineal Therapy," Ultrasound in Med & Biol., vol. 40, No. 4, pp. 804-816 (2014) (13 pages).
Barva, et al., "Parallel Integral Projection Transform for Straight Electrode Localization in 3-D Ultrasound Images," IEEE Transactions on Ultrasonics, Ferroelectrics, and Frequency Control, vol. 55, No. 7, pp. 1559-1569, Jul. 2008 (11 pages).
Ayvali, et al., "Optical Flow-Based Tracking of Needles and Needle-Tip Localization Using Circular Hough Transform in Ultrasound Images," Ann Biomed Eng, 43(8), pp. 1828-1840, Aug. 2015 (23 pages).
Beigi, et al., "Needle Trajectory and Tip Localization in Real-Time 3-D Ultrasound Using a Moving Stylus," Ultrasound in Medicine & Biology, vol. 41, No. 7, pp. 2057-2070, (2015) (14 pages).
Arif, et al., "Needle Tip Visibility in 3D Ultrasound Images," Cardiovasc Intervent Radiol 41(1), pp. 145-152 (2018) (8 pages).
Harmat, et al., "Needle Tip Localization Using Stylet Vibration," Ultrasound in Med. & BioL, vol. 3, No. 9, pp. 1339-1348 (2006) (10 pages).
Stolka, et al., "Needle Guidance Using Handheld Stereo Vision and Projection for Ultrasound-Based Interventions," Med Image Comput Comput Assist Interv, 17(Pt.2), p. 684 691 (2014) (12 pages).
Kuang, et al., "Modelling and Characterization of a Ultrasound-Actuated Needle for Improved Visibility in Ultrasound-Guided Regional Anaesthesia and Tissue Biopsy," Ultrasonics, 69, pp. 38-46 (2016) (9 pages).
Jhercik, et al., "Model Fitting Using RANSAC for Surgical Tool Localization in 3-D Ultrasound Images," IEEE Transactions on Biomedical Engineering, vol. 57, No. 8, pp. 1907-1916, Aug. 2010, (10 pages).
Torr, et al., "Mlesac: A New Robust Estimator with Application to Estimating Image Geometry," Computer Vision and Image Understanding, 78(1), pp. 138-156 (2000) (19 pages).
Fong, et al., "LSMR: An Iterative Algorithm for Sparse Least-Squares Problems," arXiv: 1006.0758v2, Jun. 10, 2011 (21 pages).
Pourtaherian, et al., "Improving Needle Detection in 3D Ultrasound Using Orthogonal-Plane Convolutional Networks," MICCAI Part2, LNCS 10434, pp. 610-618, (2017) (9 pages).
Moore, et al., "Image Guidance for Spinal Facet Injections Using Tracked Ultrasound," Med Image Comput Comput Assist Interv. Part 1, LNCS 5761, pp. 516-523 (2009) (8 pages).
Dalal, et al., "Histograms of Oriented Gradients for Human Detection," Proceedings of the 2005 IEEE Computer Society Conference on Computer Vision and Pattern Recognition (CVPR 2005) (8 pages).
Ren, et al., "Faster R-CNN: Towards Real-Time Object Detection with Region Proposal Networks," ArXiv:1506.01497v3, Jan. 6, 2016 (14 pages).

(56) References Cited

OTHER PUBLICATIONS

Afonso, et al., "Fast Image Recovery Using Variable Splitting and Constrained Optimization," IEEE Transactions on Image Processing, vol. 19, No. 9, pp. 2345-2356, Sep. 2010 (12 pages).

Agarwal, et al., "Facial Key Points Detection Using Deep Convolutional Neural Network—NaimishNet," arXiv: 1710.00977v1, Oct. 3, 2017 (7 pages).

Zhao, et al., "Evaluation and Comparison of Current Biopsy Needle Localization and Tracking Methods Using 3D Ultrasound," Ultrasonics 73, pp. 206-220 (2017) (15 pages).

Mwikirize, et al., "Enhancement of Needle Tip and Shaft from 2D Ultrasound Using Signal Transmission Maps," Medical Image Computing and Computer-Assisted Intervention—MICCAI 2016, Part 1, LNCS 9900, pp. 362-369 (2016) (8 pages).

Hatt, et al., "Enhanced Needle Localization in Ultrasound Using Beam Steering and Learning-Based Segmentation," Computerized Medical Imaging and Graphics 41, pp. 46-54 (2015) (9 pages).

Hakime, et al., "Electromagnetic-Tracked Biopsy Under Ultrasound Guidance: Preliminary Results," Cardiovasc Intervent Radiol 35(4), pp. 898-905 (2012) (8 pages).

Krucker, et al., "Electromagnetic Tracking for Thermal Ablation and Biopsy Guidance: Clinical Evaluation of Spatial Accuracy," J Vasc Interv Radiol,18(9), pp. 1141-1150, Sep. 2007 (22 pages).

Meng, et al., "Efficient Image Dehazing with Boundary Constraint and Contextual Regularization," 2013 IEEE International Conference on Computer Vision, pp. 617-624 (8 pages).

Mwikirize, et al., "Convolution Neural Networks for Real-Time Needle Detection and Localization in 2D Ultrasound," International Journal of Computer Assisted Radiology and Surgery 13(5), pp. 647-657 (2018) (11 pages).

Kirsch, "Computer Determination of the Constituent Structure of Biological Images," Computers and Biomedical Research. 4, pp. 315-328 (1971) (14 pages).

Beigi, et al., "CASPER: Computer-Aided Segmentation of Imperceptible Motion—A Learning-Based Tracking of an Invisible Needle in Ultrasound," Int J CARS, 12, pp. 1857-1866 (2017) (10 pages).

Zhao, et al., "Biopsy Needle Localization and Tracking Using ROI-RK Method," Abstract and Applied Analysis (2014) (8 pages).

Zhou, et al., "Automatic Needle Segmentation in 3D Ultra-Sound Images Using 3D Improved Hough Transform," Proceedings of SPIE Medical Imaging, vol. 6918, pp. 691821-1-691821-9 (2008) (10 pages).

Zhao, et al., "Automatic Needle Detection and Tracking in 3D Ultrasound Using an ROI-Based RANSAC and Kalman Method," Ultrasonic Imaging 35(4), pp. 283-306 (2013) (24 pages).

Arif, et al., "Automatic Needle Detection and Real-Time Bi-Planar Needle Visualization During 3D Ultrasound Scanning of the Liver," Medical Image Analysis 53, pp. 104-110 (2019) (7 pages).

Chan, et al., "Aspects of Total Variation Regularized L1 Function Approximation," Technical Report, University of California at Los Angeles (2004) (22 pages).

Chan, et al., "An Augmented Lagrangian Method for Total Variation Video Restoration," IEEE Transactions on Image Processing, vol. 20, No. 11, pp. 3097-3111, Nov. 2011 (15 pages).

Litjens, et al., "A Survey on Deep Learning in Medical Image Analysis," Medical Image Analysis, 42, pp. 60-88 (2017) (29 pages).

Lu, et al., "A New Sensor Technology for 2D Ultrasound-Guided Needle Tracking," Med Image Comput Comput Assist Interv, Part 2, LNCS 8674, pp. 389-396 (2014) (8 pages).

Redmon, et al., "Yolo9000: Better, Faster, Stronger," arXiv: 1612.08242v1, Dec. 25, 2016 (9 pages).

Miura, et al., "Visibility of Ultrasound-Guided Echogenic Needle and Its Potential in Clinical Delivery of Regional Anesthesia," Tokai J Exp Clin Med., vol. 39, No. 2, pp. 80-86 (2014) (7 pages).

Notice of Allowance dated Apr. 20, 2022, issued in connection with U.S. Appl. No. 17/268,321 (9 pages).

Applicant-Initiated Interview Summary dated Oct. 3, 2022, issued in connection with U.S. Appl. No. 16/436,284 (3 pages).

\* cited by examiner

| N | Layer name | Dimensions (W x H x D) | Kernel | Stride | Padding |
|---|---|---|---|---|---|
| 0 | input | 32 x 32 x 3 | - | - | - |
| 1 | conv_1 | 32 x 32 x 32 | 3 | 1 | 1 |
| 2 | relu_1 | 32 x 32 x 32 | - | - | - |
| 3 | maxpool | 16 x 16 x 32 | 2 | 2 | - |
| 4 | conv_2 | 16 x 16 x 32 | 3 | 1 | 1 |
| 5 | relu_2 | 16 x 16 x 32 | - | - | - |
| 6 | avgpool_1 | 8 x 8 x 32 | 2 | 2 | - |
| 7 | conv_3 | 8 x 8 x 64 | 3 | 1 | 1 |
| 8 | relu_3 | 8 x 8 x 64 | - | - | - |
| 9 | avgpool_2 | 4 x 4 x 64 | 2 | 2 | - |
| 10 | fc_1 | 1 x 1 x 64 | - | - | - |
| 11 | relu_4 | 1 x 1 x 64 | - | - | - |
| 12 | fc_detection | 1 x 1 x 2 | - | - | - |
| 13 | softmax | - | - | - | - |
| 14 | classification | - | - | - | - |

FIG. 5

Input: US image $I(x, y)$
Output: Tip location $(x_t, t_t)$, Enhanced shaft image $I_e(x, y)_{shaft}$ (1.1) $G(v, e) \leftarrow I(x, y)$ △ $G(v, e)$ is an 8-connected graph
(1.2) $W_h, W_v, W_d \leftarrow e_{ij}$ △ $e_{ij}$ are edges, $W_h, W_v, W_d$ are edge dependent weights
(1.3) $I_c(x, y) \leftarrow W$ △ confidence map $I_c(x, y)$ from graph weights
(1.4) $\Psi(x, y)_{tip} \leftarrow I_c(x, y)$ △ $\Psi$ is patch-wise transmission function
(2.1) $W_p \leftarrow I(x, y)$ △ $W_p$ are contextural weights
(2.2) $t(x, y)_{tip} \leftarrow \Psi(x, y)_{tip}$ △ regularization, $t(x, y)_{tip}$ is signal transmission map (tip)
(3.1) $v \leftarrow I(x, y)$ △ v is echogenicity of tissue confining the needle
(3.2) $I_e(x, y) \leftarrow I(x, y)$ △ needle restoration model for tip enhancement
(4) $I_e(x, y) - (I_e(x, y) \ominus L) \oplus L \leftarrow I_e(x, y)$ △ Top-hat filter, L is a linear element
(5.1) $I(\theta) \leftarrow I_e(x, y)_{tip}$ △ Local phase-based filtering
(5.2) $I_{\theta+\theta_o} \leftarrow I(\theta)$ △ $I_\theta$ is a linear trajectory mask
(5.3) $I(\theta, l) \leftarrow I_{\theta+\theta_o}$ △ pixels in $I_e(x, y)_{tip}$ lying along trajectory
(5.4) $I(\theta, l) - I(\theta_o, l_o) \leftarrow I(\theta, l)$ △ remove outliers to leave only candidate pixels
(5.5) $(x_t, t_t) \leftarrow$ candidate pixels △ geometrical optimization and intensity search
(6.1) $\Psi(x, y)_{shaft} \leftarrow I_{\theta+\theta_o}$
(6.2) $t(x, y)_{shaft} \leftarrow \Psi(x, y)_{shaft}$ △ patch-wise transmission map for shaft
   △ regularization
(6.3) $I_e(x, y)_{shaft} \leftarrow t(x, y)_{shaft}$ △ needle restoration model for shaft enhancement

FIG. 17

COMPUTER VISION SYSTEMS AND METHODS FOR REAL-TIME NEEDLE DETECTION, ENHANCEMENT AND LOCALIZATION IN ULTRASOUND

RELATED APPLICATIONS

This application is a continuation application of and claims priority to U.S. Provisional Patent Application No. 62/682,456 filed on Jun. 8, 2018, the entire disclosure of which is expressly incorporated herein by reference.

BACKGROUND

Technical Field

The present disclosure relates generally to the field of computer vision technology. More specifically, the present disclosure relates to computer vision systems and methods for real-time needle detection, enhancement and localization in ultrasound.

Related Art

Minimally invasive procedures such as regional anesthesia and interventional oncology involve the insertion of a needle toward target anatomy. In practice, image guidance is used to improve targeting accuracy. Of all imaging modules, ultrasound ("US") is ubiquitously used due to its real-time, low-cost and radiation-free capabilities. However, with the conventional 2D ultrasound, aligning the needle with the ultrasound imaging plane at steep angles and deep insertions is difficult.

Therefore, there is a need for computer vision systems and methods for real-time needle detection, enhancement and localization in ultrasound, thereby improving the ability of computer vision systems to detect a needle at steep angles and deep insertions. These and other needs are addressed by the computer vision systems and methods of the present disclosure.

SUMMARY

The present disclosure relates to computer vision systems and methods for real-time needle detection, enhancement and localization in ultrasound. In a first embodiment, the computer vision system will detect a placement of an object in a digital image. Specifically, the computer vision system will perform a needle detection phase, a needle trajectory localization phase, and a tip localization phase. In a second embodiment, the computer vision system will enhance and localize a steeply inserted needle. Specifically, the computer vision system will perform a tip enhancement phase, a tip localization phase, and a shaft enhancement phase. In a third embodiment, the computer vision system will automatically detect and enhance needles under 3D ultrasound guidance. Specifically, the computer vision system will perform a needle detection phase, a needle enhancement phase, and a tip localization phase.

BRIEF DESCRIPTION OF THE DRAWINGS

The foregoing features of the invention will be apparent from the following Detailed Description of the Invention, taken in connection with the accompanying drawings, in which:

FIG. 5 is a table illustrating an example architecture of the fast R-CNN;

FIGS. 16-17 is a diagram illustrating the tip enhancement phase, the tip localization phase and the shaft enhancement phase;

DETAILED DESCRIPTION

The present disclosure relates to computer vision systems and methods for real-time needle detection, enhancement and localization in ultrasound as described in detail below in connection with FIGS. 1-35.

Figure 1:
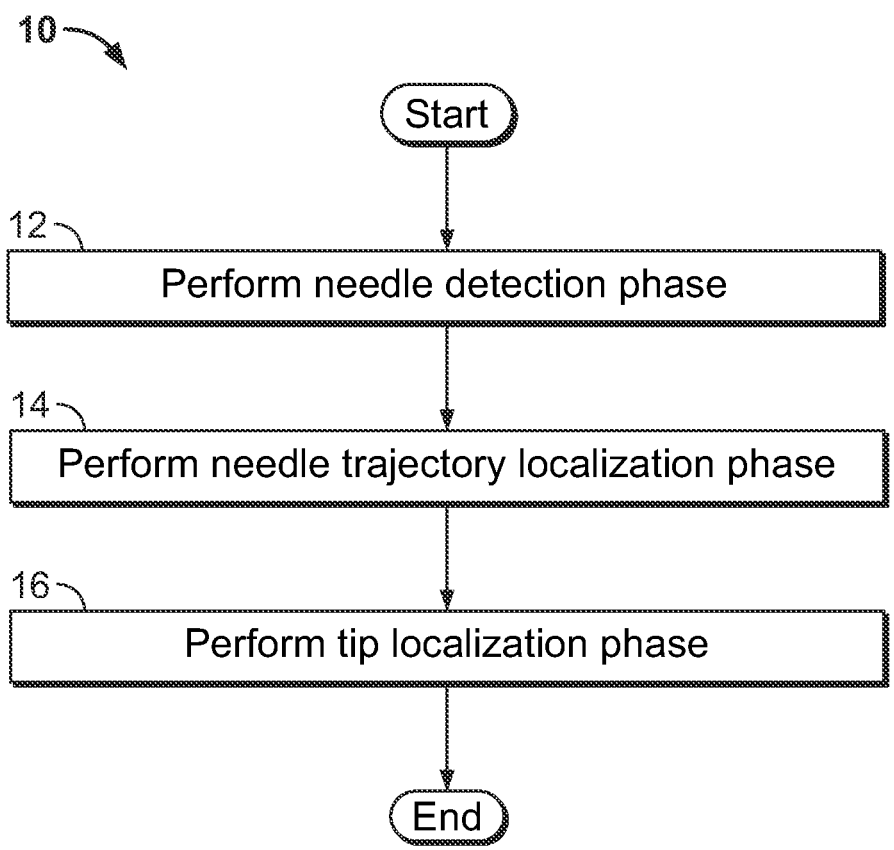
FIG. 1 is a flowchart illustrating overall process steps carried out by a first embodiment of the system of the present disclosure.

FIG. 1 shows a flowchart illustrating overall process steps being carried out by a first embodiment of the system of the present disclosure, indicated generally at 10. Specifically, method 10 will detect a placement of an object in a digital image. The digital image can be a ultrasound image, a magnetic resonance imaging ("MRI") image, a functional MRI ("fMRI") image, a nuclear magnetic resonance ("NMR") image, a positron emission tomography ("PET") scan image, a computer tomography ("CT") image, an X-ray image, or any other related image. The embodiments described below relate to ultrasound images. It should be understood that any reference to the ultrasound image is only by way of example and that the systems, method and embodiments discussed throughout this disclosure may be applied to any image, including, but not limited to, the digital images listed above. Furthermore, the object in the digital image can be a needle, a catheter, a probe, a measurement tool, a medical implant, a medical rod, or any other insertable object. The embodiments described below will be related to a needle and will refer to the object as a needle. It should be understood that any reference to the needle is only by way of example and that the systems, method and embodiments discussed throughout this disclosure may be applied to any object, including but not limited to the objects listed above.

In step 12, the system performs a needle detection phase. The needle detection phase uses one or more convolutional neural networks ("CNN") to detect the needle. A neural network, such as a CNN, is a multiple layer network with learnable weights and biases that can be used for, among other things, analyzing visual imagery. CNNs are widely used in machine learning and are an effective tool in various image processing tasks, such as classification of objects. In particular, CNNs can be used as feature extractors to extract different details from images to identify objects in the digital images. In step 14, the system performs a needle trajectory localization phase. In step 16, the method performs a tip localization phase.

CNNs will be discussed and referenced in this disclosure by way of example. It should be understood that those skilled in the art are capable of adapting the systems and methods discussed herein to use other machine learning systems, including, but not limited to, deep neural networks ("DNNs"), recurrent neural networks ("RNNs"), etc. For example, a DNN using a deep learning based method and the methods discussed herein can detect a placement of an object, such as a needle, in a digital image, such as an ultrasound image, while also reducing irrelevant background and/or background noise.

It should be understood that FIG. 1 is only one potential configuration, and the system of the present disclosure can be implemented using a number of different configurations. The process steps of the invention disclosed herein could be embodied as computer-readable software code executed by one or more computer systems, and could be programmed using any suitable programming languages including, but not limited to, C, C++, C#, Java, Python or any other suitable language. Additionally, the computer system(s) on which the present disclosure may be embodied includes, but is not limited to, one or more personal computers, servers, mobile devices, cloud-based computing platforms, etc., each having one or more suitably powerful microprocessors and associated operating system(s) such as Linux, UNIX, Microsoft Windows, MacOS, etc. Still further, the invention could be embodied as a customized hardware component such as a field-programmable gate array ("FPGA"), application-specific integrated circuit ("ASIC"), embedded system, or other customized hardware component without departing from the spirit or scope of the present disclosure.

Figure 2:
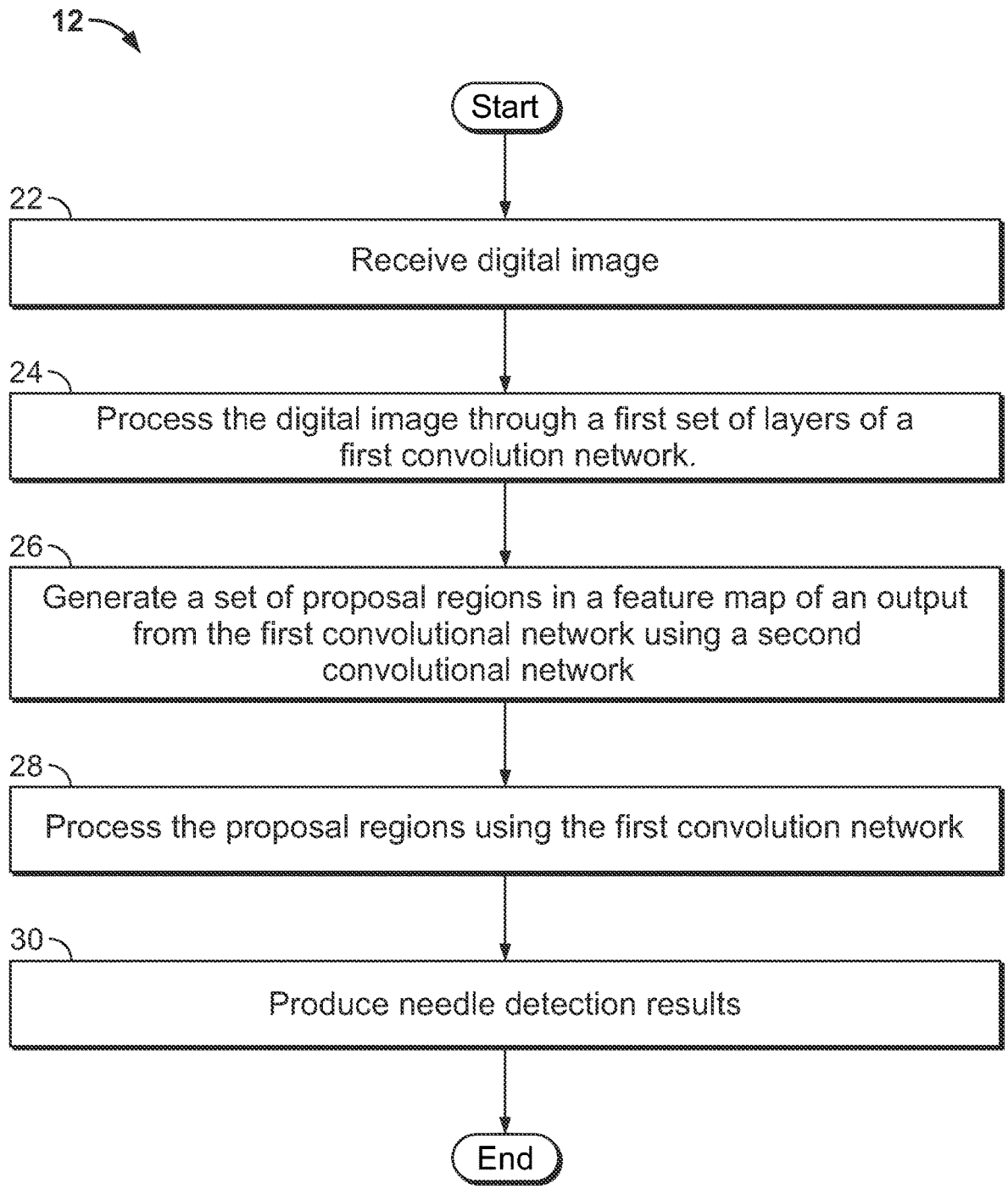
FIG. 2 is a flowchart illustrating step 12 of FIG. 1 in greater detail.

FIG. 2 shows a flowchart illustrating step 12 of FIG. 1 in greater detail. In particular, FIG. 2 illustrates process steps performed during the needle detection phase 12. In step 22, the system receives an input image. For example, the system receives a digital image, such as an ultrasound image. A size of the input image size can be chosen to be similar to a smallest detectable object. For example, a 32×32×3 input image is chosen. The image may be preprocessed. For example, ultrasound images from minimally invasive procedures such as biopsies and epidural spinal injections may contain high-intensity artifacts which increase the likelihood of false positives, thus reducing accuracy of needle detection. Preprocessing the image can reduce the influence of the artifacts. In an example, the system can subject a B-mode image I (x, y) to a Top-hat filter using a linear structuring element L (x, y), and the filtered image F (x, y)=I (x, y)−[I (x, y) o L (x, y)], where I (x, y) o L (x, y) denotes an erosion operation.

Figure 3:
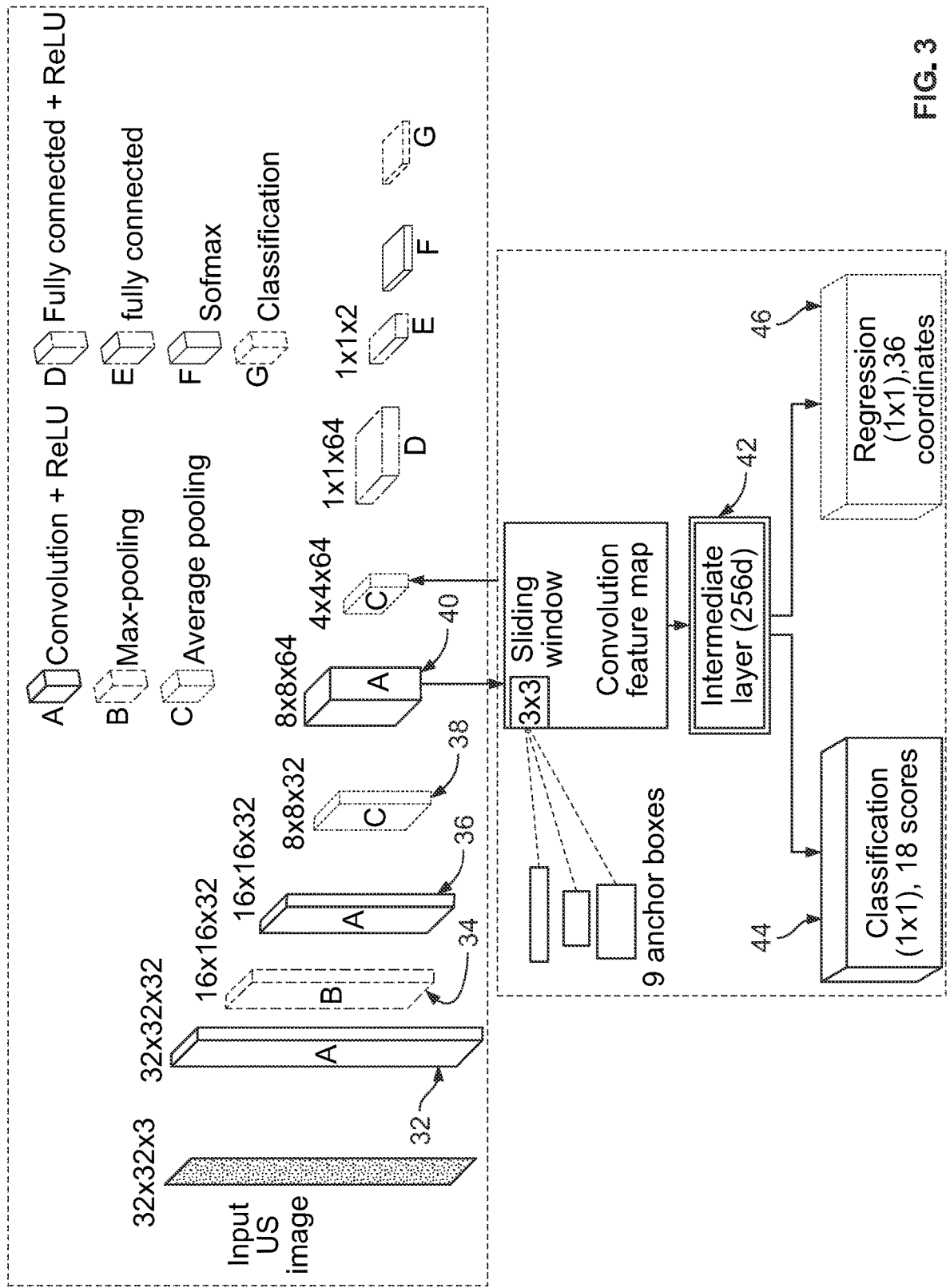
FIG. 3 is a diagram illustrating the layers of the first convolution network and a second convolution network.
Figures 4A, 4B:
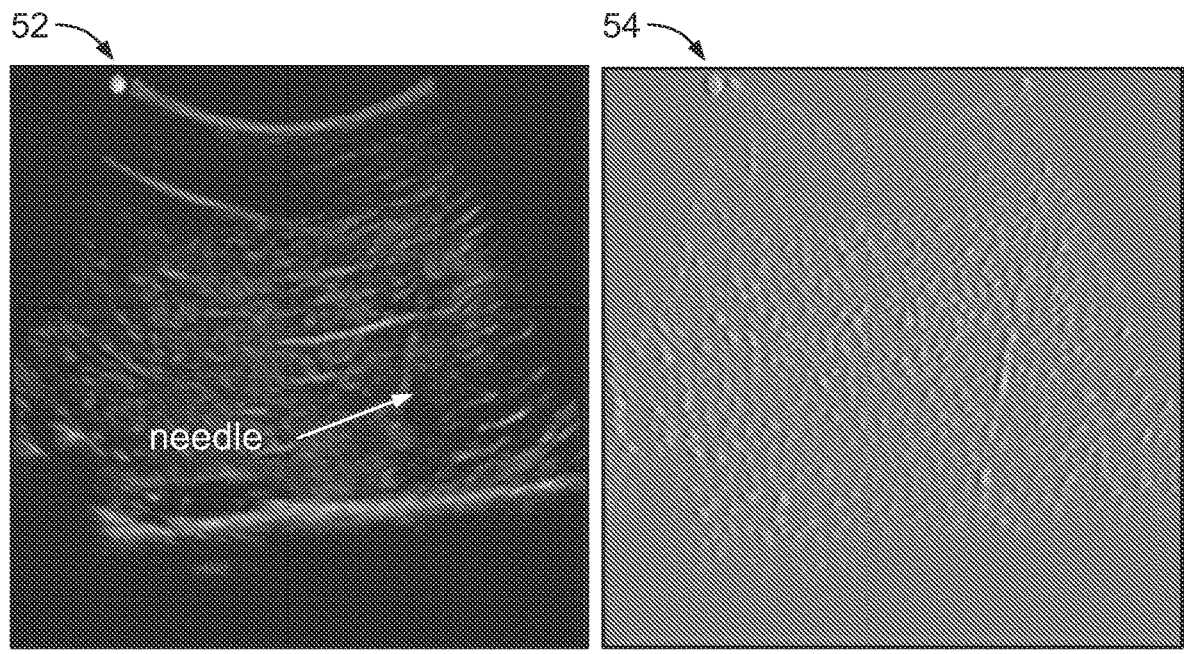
FIGS. 4A, 4B, 4C, and 4D are images illustrating a digital image and feature maps from convolution layers.
Figures 4C, 4D:
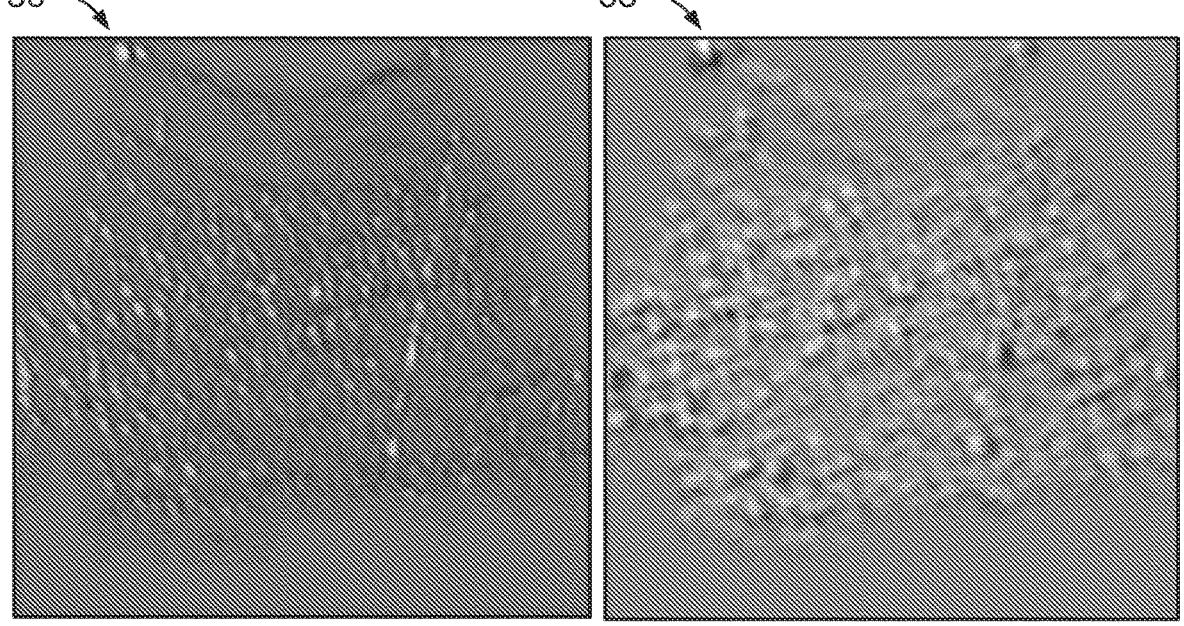

In step 24, the system processes the digital image through a first set of layers of a first convolution network. The process is illustrated in FIG. 3, which is an illustration showing the layers of the first convolution network and a second convolution network. As shown in FIG. 3, the first set of layers includes convolution layer 1 (32), max pooling layer 1 (34), convolution layer 2 (36), average pooling layer 1 (38), and convolution layer 3 (40). In an example, convolution layer 1 (32) learns the distinct linear features specific to the needle, while convolution layer 2 (36) and convolution layer 3 (40) learn semantic features associated with the needle. A linear feature refers to a coarse and correctly orientated line-like structure (such as, for example, a needle) in the digital image (e.g., ultrasound image). A semantic feature refers to information that gives finer grain inference on the needle. This can include needle tip data, additional data relating to needle dimensions, etc. Semantic features can provide can be more relied upon when needle shaft data is scantily available. Those skilled in the art would understand that any number of layers can be included in the first set of layers. FIG. 4A illustrates an example of a digital image 52, FIG. 4B illustrates a feature map from convolution layer 1 (54), FIG. 4C illustrates a feature map from convolution layer 2 (56), and FIG. 4D illustrates a feature map from convolution layer 3 (58). The first convolutional network can be a fast region-based convolutional neural network ("R-CNN"). Further, FIG. 5 illustrates an example architecture of the fast R-CNN. Those skilled in the art would understand that a different architecture can be used, which includes one or more of, a different number of layers, different layer types, different dimension, etc.

Returning to FIG. 2, in step 26, the system generates a set of proposal regions in a feature map of an output from the first convolutional network using the second convolutional network. The output is from a last layer of the first set of layers (e.g., convolution layer 3). The one or more regions can be, for example, regions of interest. The second convolutional network can be a regional proposal network ("RPN"). The RPN can generate the one or more regions of interest by ranking potential bounding boxes for the needle (e.g., anchors).

Figure 6:
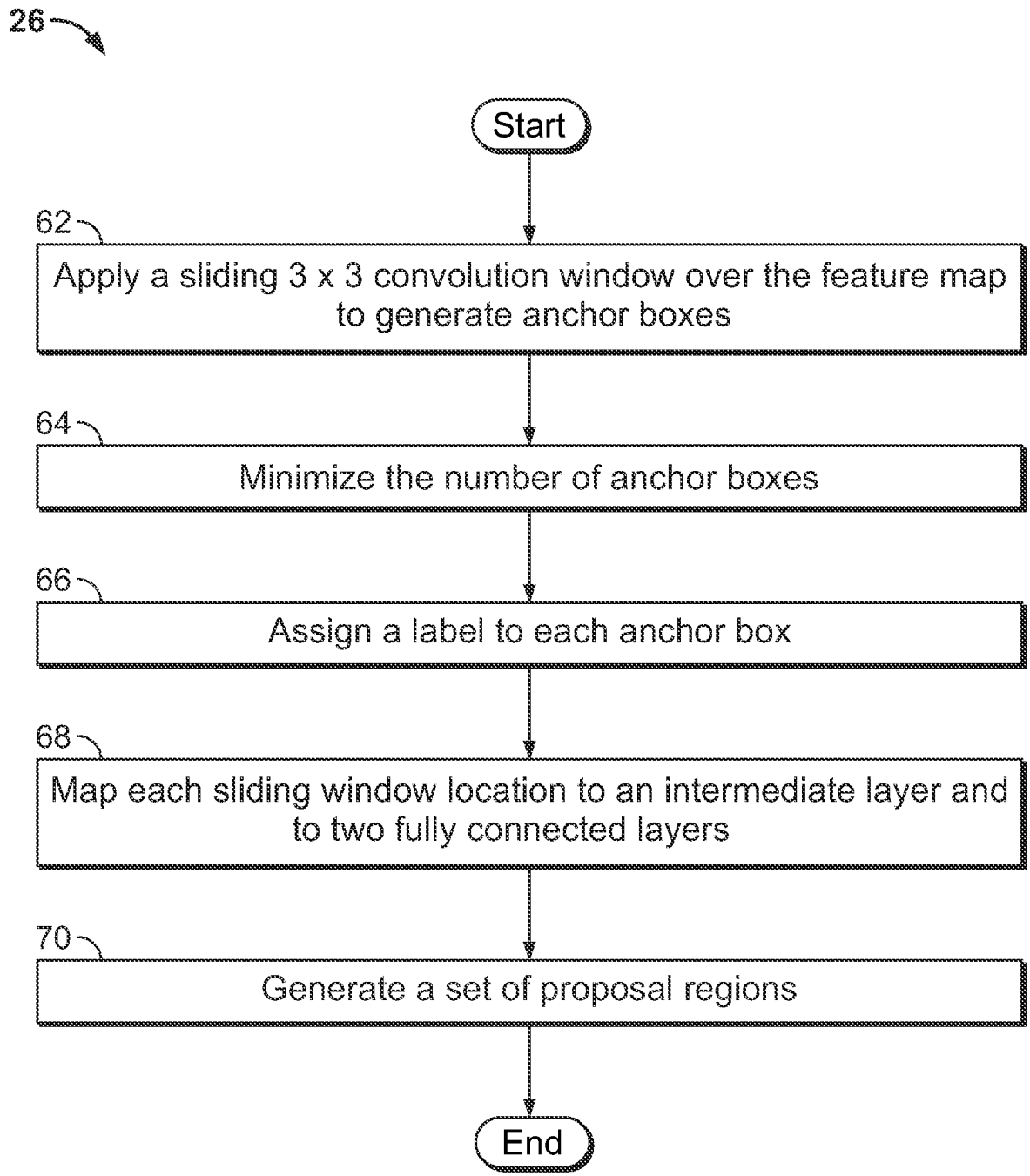
FIG. 6 is a flowchart illustrating step 26 of FIG. 2 in greater detail.

FIG. 6 shows a flowchart illustrating step 26 of FIG. 2 in greater detail. In particular, FIG. 6 illustrates process steps performed to generate the areas of interest. In step 62, the system applies a sliding 3×3 convolution window over the feature map to generate anchor boxes. At each window, a maximum of 9 anchor boxes are predicted, generated from 3 scales with a scaling stride of 1.5×($d_m$, 1.5×$d_m$, 2.25×$d_m$) and three aspect ratios (1:1, 1:2, 2:1), where $d_m$ corresponds to the minimum dimension of the bounding boxes in the labeled training images. For a feature map of size w×h, the maximum number of anchor boxes is equal to w×h×9. In this example, the maximum number of anchor boxes is about 600.

In step 64, the system minimizes the number of anchor boxes. In an example, the system eliminates cross-boundary anchor boxes. This will leave approximately 60 anchor boxes per ultrasound image. In step 66, the system assigns a label to each anchor box. For example, the system can assign a positive class label (which indicates a needle is present) when the intersection-over-union ("IoU") overlap with the needle bounding box in a labeled ultrasound image is greater than 0.7. The system can further assign a negative class label (which indicates no needle is present) if the IoU is less than 0.7. By assigning a class label to each anchor box, the system detects whether a region centered at each sliding window location contains needle data, and the sliding window location encodes coarse localization information with reference to an input ultrasound image.

In step 68, the system maps each window location to an intermediate layer and to two fully connected layers. The intermediate layer can be a 256-dimensional intermediate layer. The two fully connected layers can be two sibling 1×1 fully connected layers, shared across all sliding window locations, for box-classification (e.g., needle or no needle) and box-regression (e.g., for finer localization information). This is also illustrated in FIG. 3, which shows a intermediate layer 42, a classification layer 44, and a regression layer 46. In an example, the classification layer can output a maximum of 18 scores, and the regression layer can output a maximum of 36 outputs encoding coordinates of the 9 anchor boxes, for each sliding window location. The outputs of the fully connected layers can be determined by minimizing an RPN multi-task loss function, by using the following formula:

$$L(p_j, p_j^*, t_j, t_j^*) = \frac{1}{N_c}\sum_j L_c(p_j, p_j^*) + \frac{\lambda}{N_r}\sum_j p_j^* L_r(t_j, t_j^*)$$

The first term of the above formula describers a box-classifier and the second term of the above formula describes the box aggressor. An anchor index is represented by j, $p_j$ denotes an associated predicted probability, and $t_j$ is the predicted location. A ground-truth label arising from IoU scores is denoted by $p^*_j \in [0, 1]$, and $t^*_j$ denotes an associated location. $\lambda$ denotes a regularization parameter. $L_c$ denotes a log loss over two classes (needle and no needle), and $L_r$ denotes a regression loss. $L_r$ is a smooth $L_1$ loss, which is denoted by the following formula:

$$L_r(t, t^*) = \begin{cases} 0.5(t-t^*)^2, & \text{if } |t-t^*| < 1 \\ |t-t^*| - 0.5, & \text{otherwise} \end{cases}$$

In an example, $N_c$ is set to 256, $N_r$ is set to 600 (the approximate number of total anchor boxes locations, and the regularization parameter $\lambda$ is set to 10). Since the derived RPN proposals may overlap, the system uses a non-maximum suppression based on $p_j$, using a threshold of 0.8. In step 60, the system generates a set of proposal regions. In an example, the proposal regions are top-N ranked.

Figure 7A:
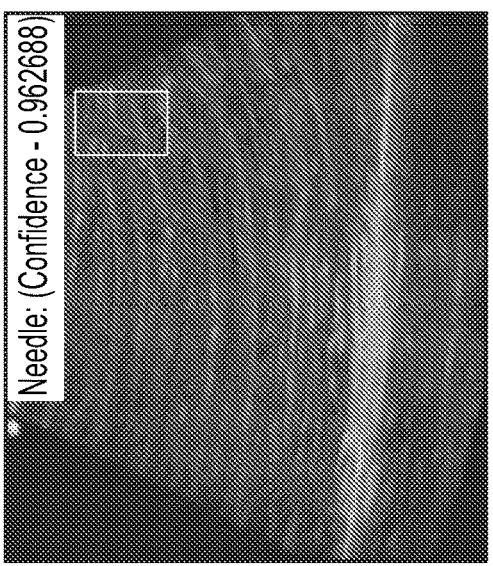
FIGS. 7A, 7B, 7C, 7D, 7E, and 7F are images illustrating needle detection results.
Figure 7B:
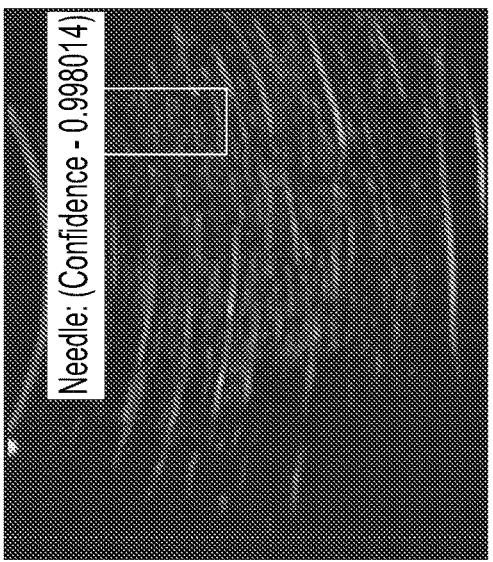
Figure 7C:
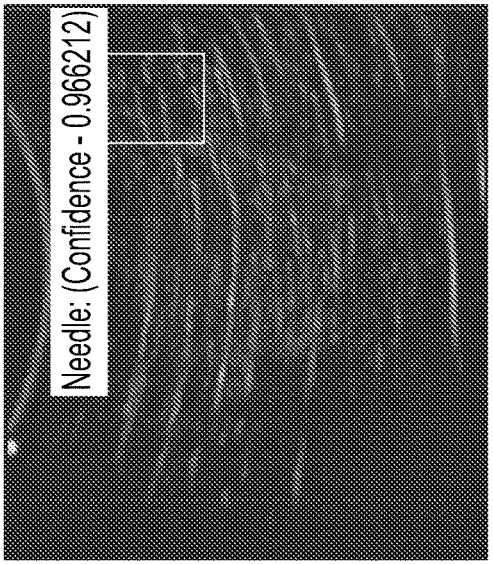
Figure 7D:
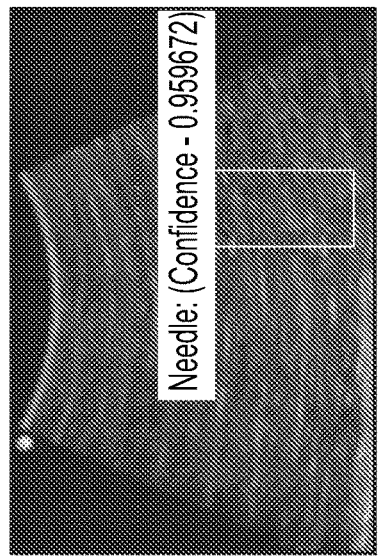
Figure 7E:
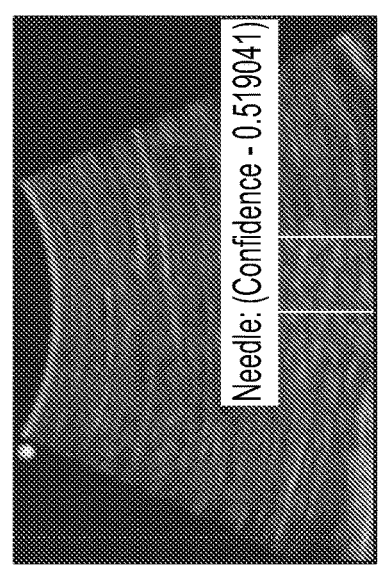
Figure 7F:
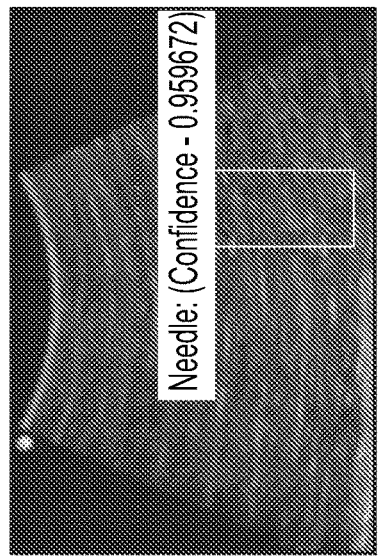
Figure 8B:
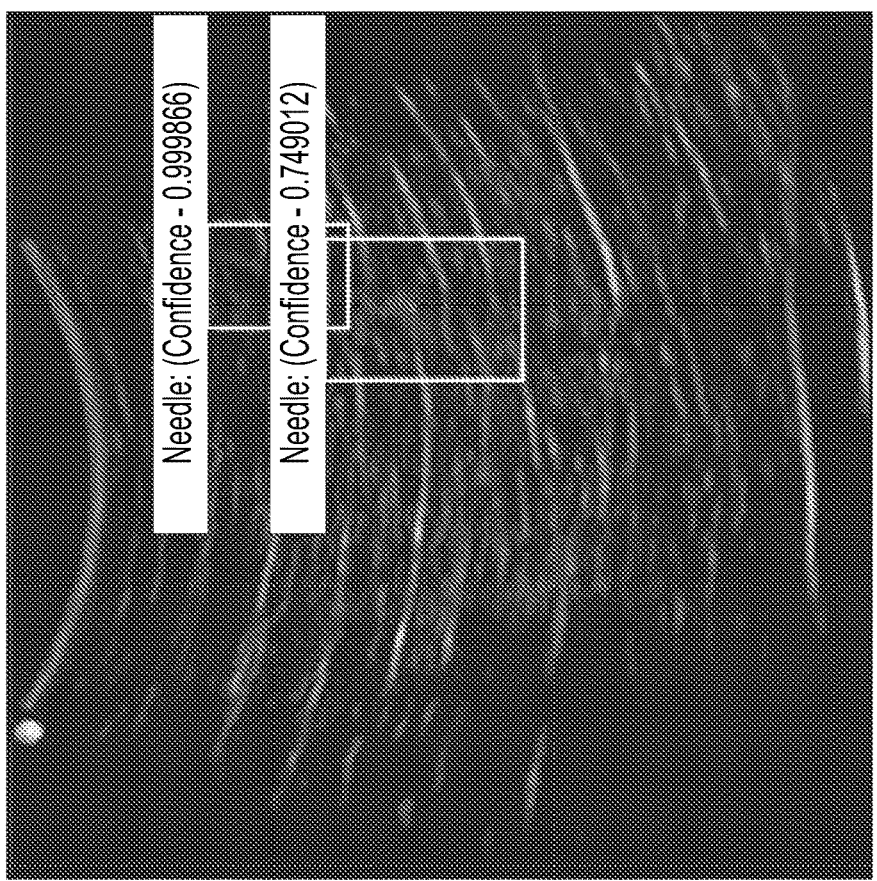
FIGS. 8A-8B are images illustrating needles in an ultrasound image.
Figure 8A:
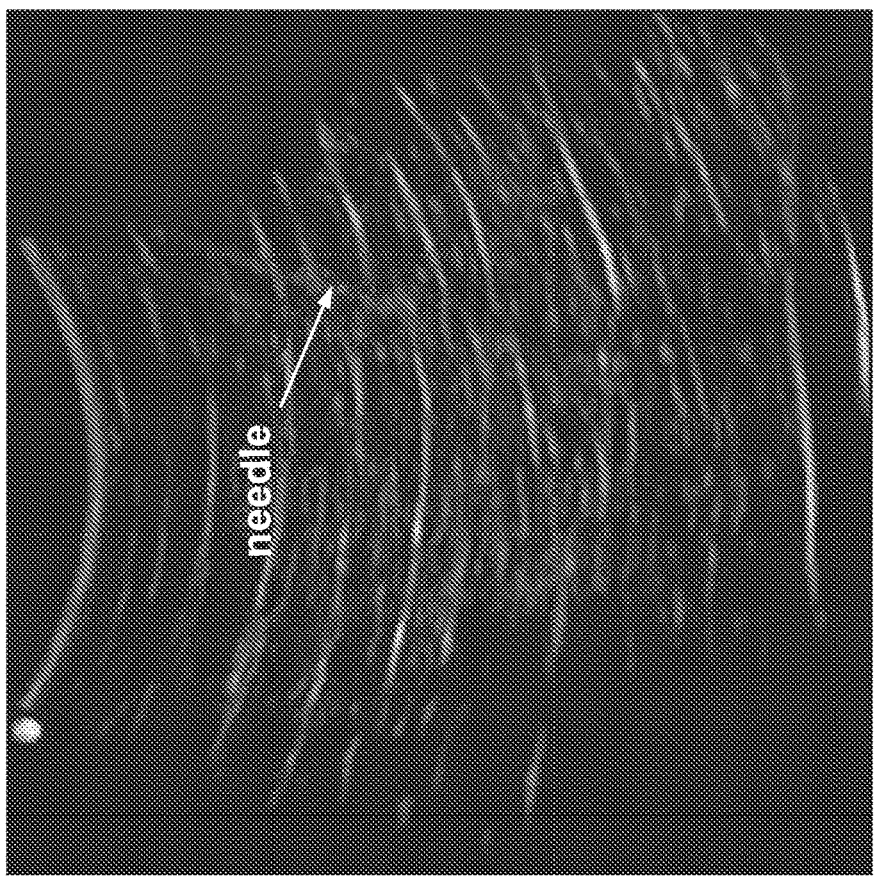

Returning to FIG. 2, in step 28, the system processes the proposal regions using the first convolution network (e.g., the fast R-CNN). Specifically, the R-CNN generates an overall classification and tightened bounding boxes. In step 30, the system produces needle detection results. The needle detection results can include a marked region or interest with a detection score. This is shown in FIGS. 7A, 7B, 7C, 7D, 7E, and 7F, which illustrate images of the needle detection results. The needle shaft is accurately localized, despite, for example, low needle shaft intensity (as seen in FIGS. 7A, 7B, and 7C) or imperceptible needle shaft intensity (as seen in the bottom row of FIGS. 7D, 7E, and 7F). The numbers associated with the bounding boxes in FIGS. 7A-F are the detection score(s). The detection scores are a measure of the confidence of detection. When multiple detection exist, the system selects the highest detection score. FIG. 8A shows an image of a needle in an ultrasound image, and FIG. 8B shows an image of two needle detections for a same needle, each with a confidence score. Again, the system selects the highest detection score.

To achieve a unified network, the RPN and the fast R-CNN can be trained using a 4-step alternating process. In step 1, the RPN is trained end-to-end. In step 2, the fast R-CNN is trained using region proposals derived from step 1. In step 3, the RPN is retrained using shared weights of the fast R-CNN from step 2. In step 4, while keeping the shared layers fixed, the fast R-CNN is retrained using the updated region proposals from step 3.

Figure 9:
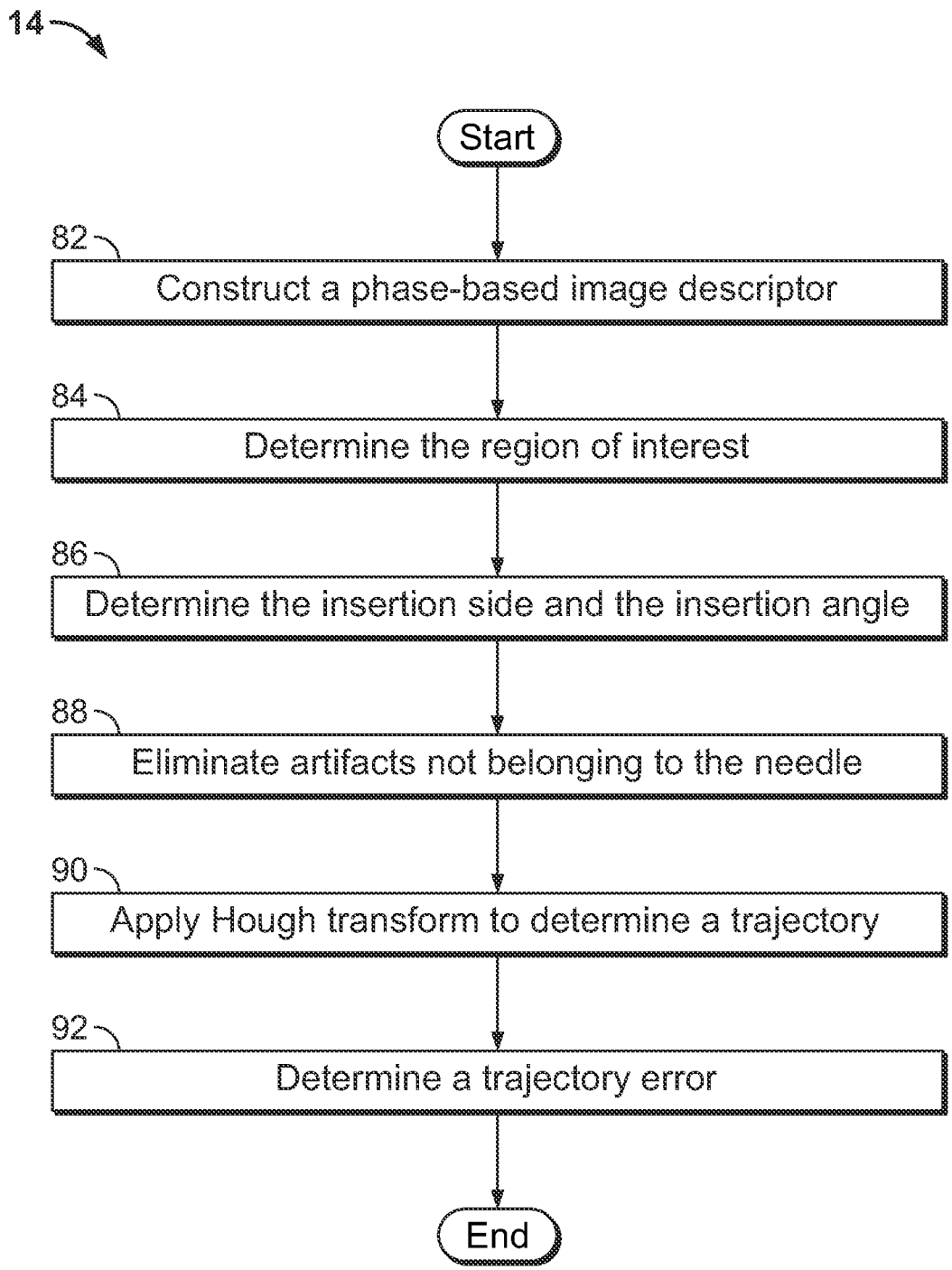
FIG. 9 is a flowchart illustrating step 14 in greater detail.

FIG. 9 shows a flowchart illustrating step 14 of FIG. 1 in greater detail. In particular, FIG. 9 illustrates process steps performed during the needle trajectory localization phase. In step 82, the system constructs a phase-based image descriptor (phase symmetry (PS (x, y))). In an example, the phase-based image descriptor is constructed using an orientation-tuned 2D Log-Gabor filter bank applied to the marked region of interest on an ultrasound image (e.g., the output from the fast R-CNN). A function of the filter bank is denoted as follows:

$$LG(\omega, \theta) = \exp\left(\frac{-\log\left(\frac{\omega}{\kappa}\right)^2}{2\log(\sigma_\omega)^2}\right)\exp\left(\frac{-(\theta-\theta_m)^2}{2(\sigma_\theta)^2}\right)$$

Frequency/orientation coordinates are denoted as (ω, θ), k is a center frequency, $\sigma_\omega$ is a bandwidth of the frequency spectrum, $\sigma_\theta$ is an angular bandwidth, and $\theta_m$ is a specific filter orientation. The filter parameters can be either tuned or based on priori data. For example, the priori data can include an estimate of the needle trajectory or insertion side of the needle (for $\theta_m$) and a fixed region of interest containing the shaft, close to a transducer surface.

In step 84, the system determines a region of interest. In an example, the region of interest corresponds to the needle bounding box from the needle detection phase. In step 86, the system determines an insertion side and an insertion angle. In an example, the system determines the insertion side and the insertion angle from the bounding box. Specifically, the system defines the bounding box with parameters $x_i$, $y_i$, L, and W. The system then sets $(x_c, y_c)$ as a center of the ultrasound image. For right side insertions, $x_i < x_c$, and an estimate of the needle trajectory, β is given by β=tan$^{-1}$ (W/L). For left side insertions, $x_i > x_c$, and an estimate of the needle trajectory, β is given by β=90+tan$^{-1}$ (W/L). The filter bank is applied with 3 scales and 3 orientations. $\Theta_m$=[β−10, β, β+10], and yields a PS (x, y) image containing a prominent needle feature.

In step 88, the system eliminates artifacts not belonging to needle from the PS (x, y) image. In an example, the system extracts the longest connected component. This yields a $PS_L$ (x, y) image, which includes a distinct, intensity invariant straight feature. In step 90, the system applies Hough transform ("HT") to the ultrasound image to determine the trajectory. In step 92, the system determines a trajectory error. In an example, the system determines the trajectory error by comparing the determined trajectory with a gold-standard trajectory estimated by an expert sonographer. For example, the system can denote an original ultrasound image as I $(x, y)_{m \times n}$ where m and n are horizontal and vertical dimensions, and the center of the image is estimated as $(x_c, y_c)$=(m/2, n/2). The system then calculates an angle subtended by the automatically detected trajectory on the horizontal axis ($\gamma_1$), an angle subtended by the trajectory labeled by an expert on the horizontal axis ($\gamma_2$), a shortest distance between the detected trajectory and the center of the image ($\lambda_1$), and a shortest distance between the expert-labeled trajectory and the center of the image ($\lambda_2$). The trajectory error is then quantified using $\gamma_1 - \gamma_2$ and $\lambda_1 - \lambda_2$.

Figure 10A:
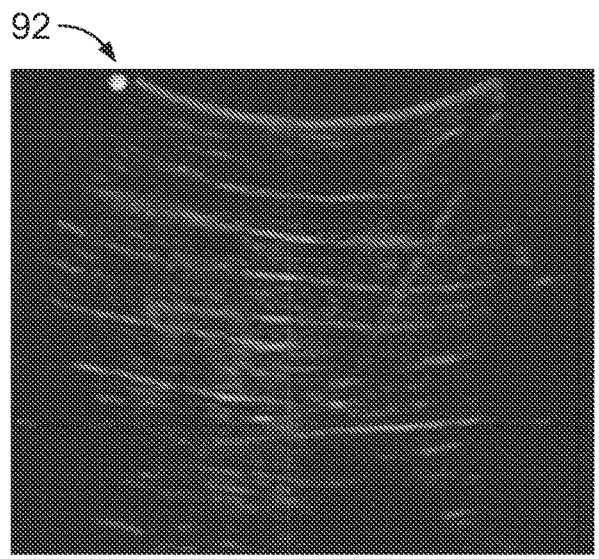
FIGS. 10A, 10B, 10C, and 10D are images illustrating a needle trajectory estimation.
Figure 10B:
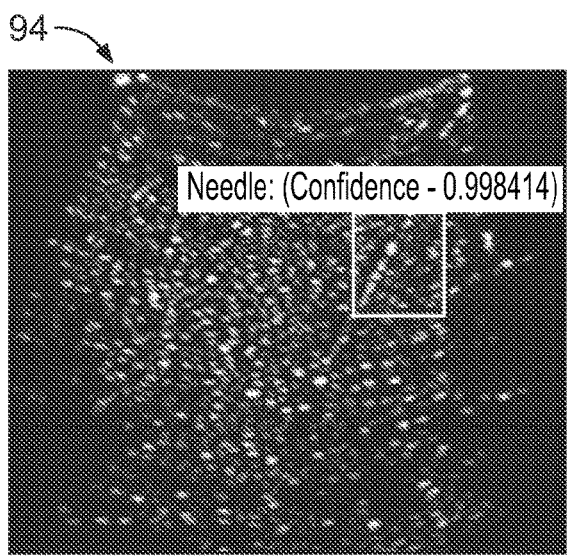
Figure 10C:
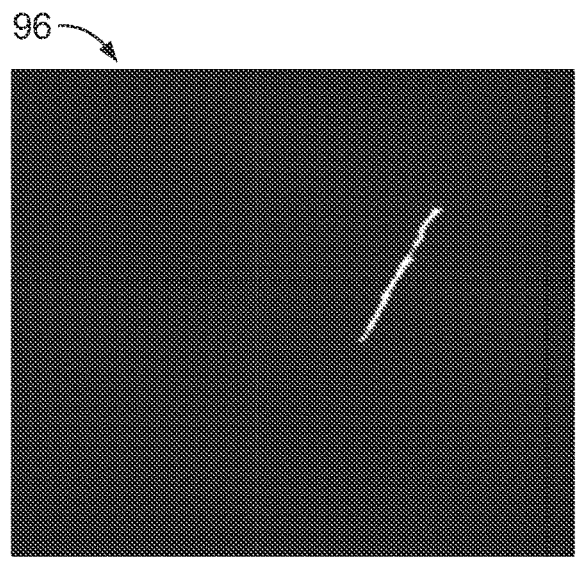
Figure 10D:
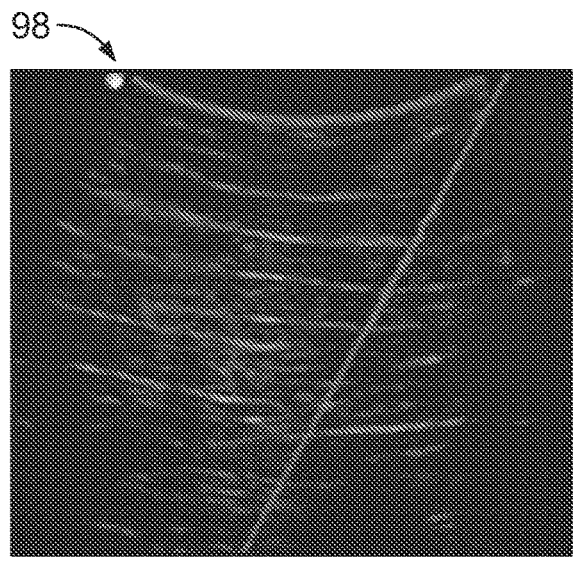

FIGS. 10A, 10B, 10C, and 10D are images showing a needle trajectory estimation. FIG. 10A is an illustration 92 showing ultrasound image, FIG. 10B is an illustration 94 showing a preprocessed image with a marked region of interest, FIG. 10C is an illustration 96 showing an image after the extraction of local-phase features and a determined longest connected component, and FIG. 10D is an illustration 98 showing an estimated trajectory after applying the Hough transform.

Figure 11:
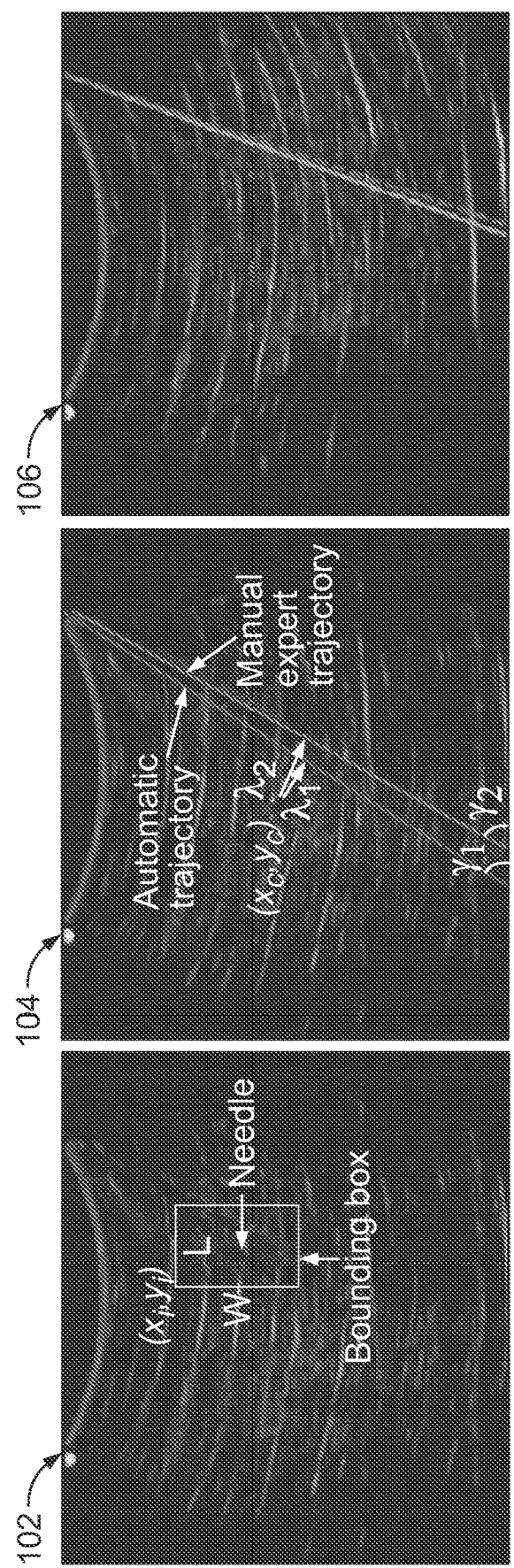
FIG. 11 is a set of images illustrating a prediction of a needle trajectory.

FIG. 11 is an illustration showing a prediction of a needle trajectory. Illustration 102 shows an estimation of needle insertion side and trajectory. Illustration 104 shows the parameters use in calculating needle trajectory error. Illustration 106 shows a trajectory from the method described in step 14 in solid line, and an expert-labeled overlaid on an ultrasound image in dashed line.

Figure 12:
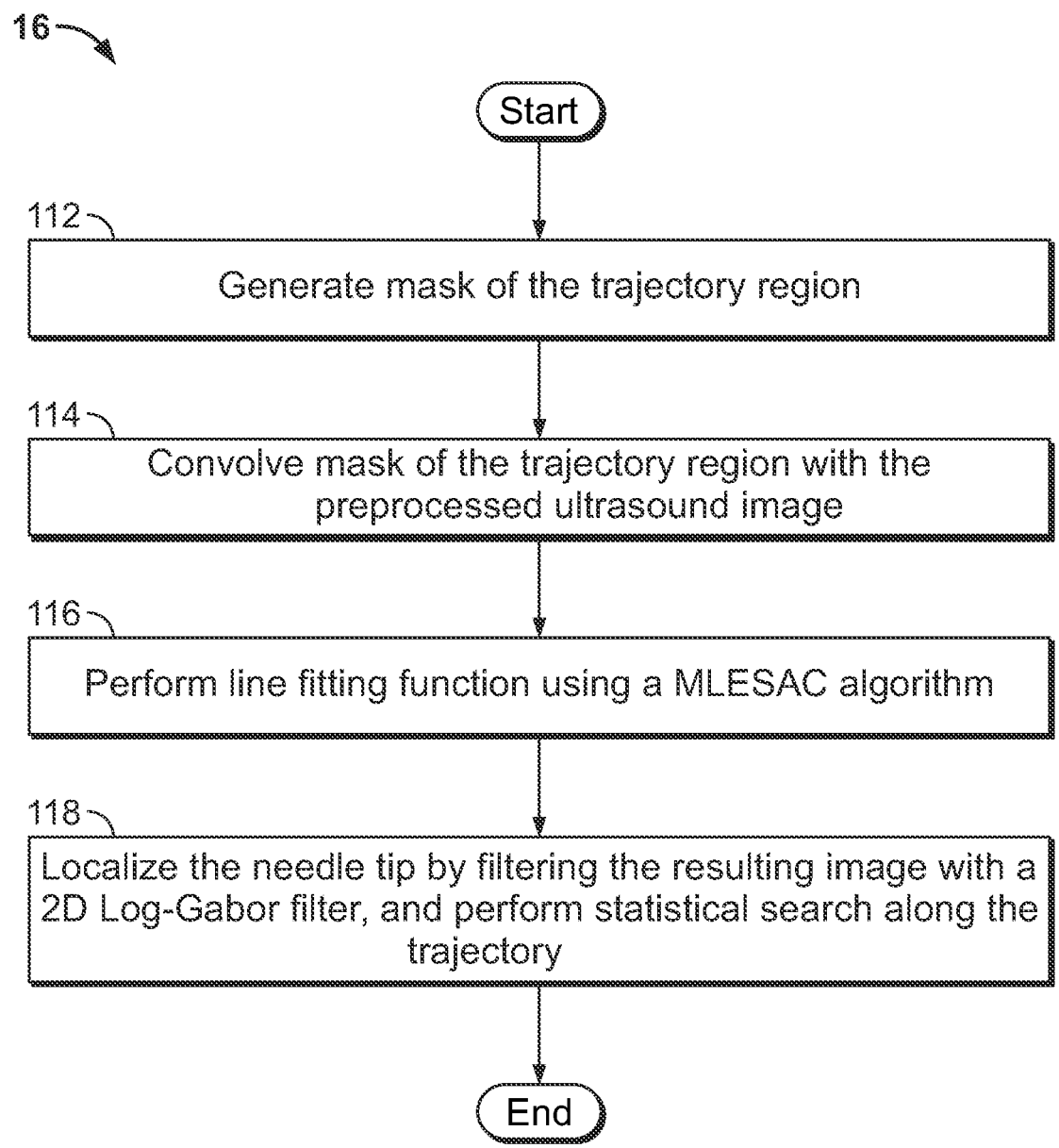
FIG. 12 is a flowchart illustrating step 16 of FIG. 1 in greater detail.

FIG. 12 shows a flowchart illustrating step 16 of FIG. 1 in greater detail. In particular, FIG. 12 illustrates process steps performed during the tip localization phase. In step 112, the system generates a mask of the trajectory region. In step 114, the system convolves a mask of the trajectory region with the preprocessed ultrasound image. In step 116, the system performs a line fitting function using a maximum likelihood estimation sample and consensus ("MLESAC") algorithm. In step 118, the system localizes the needle tip by filtering the resulting image with a 2D Log-Gabor filter, and performs a statistical search along the trajectory line.

Figure 13:
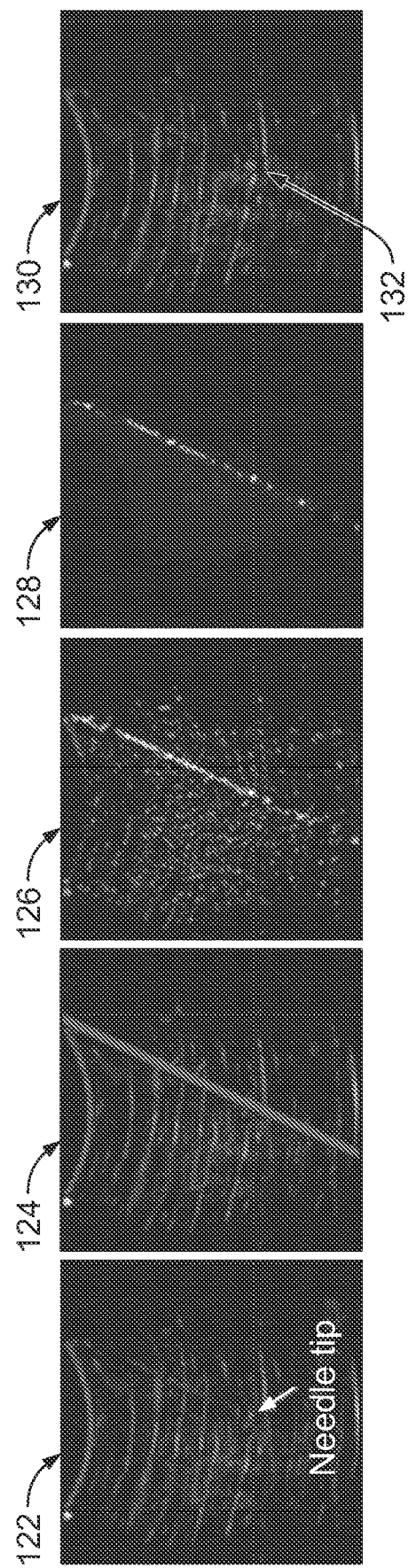
FIGS. 13-14 are images illustrating the needle tip localization process.
Figure 14:
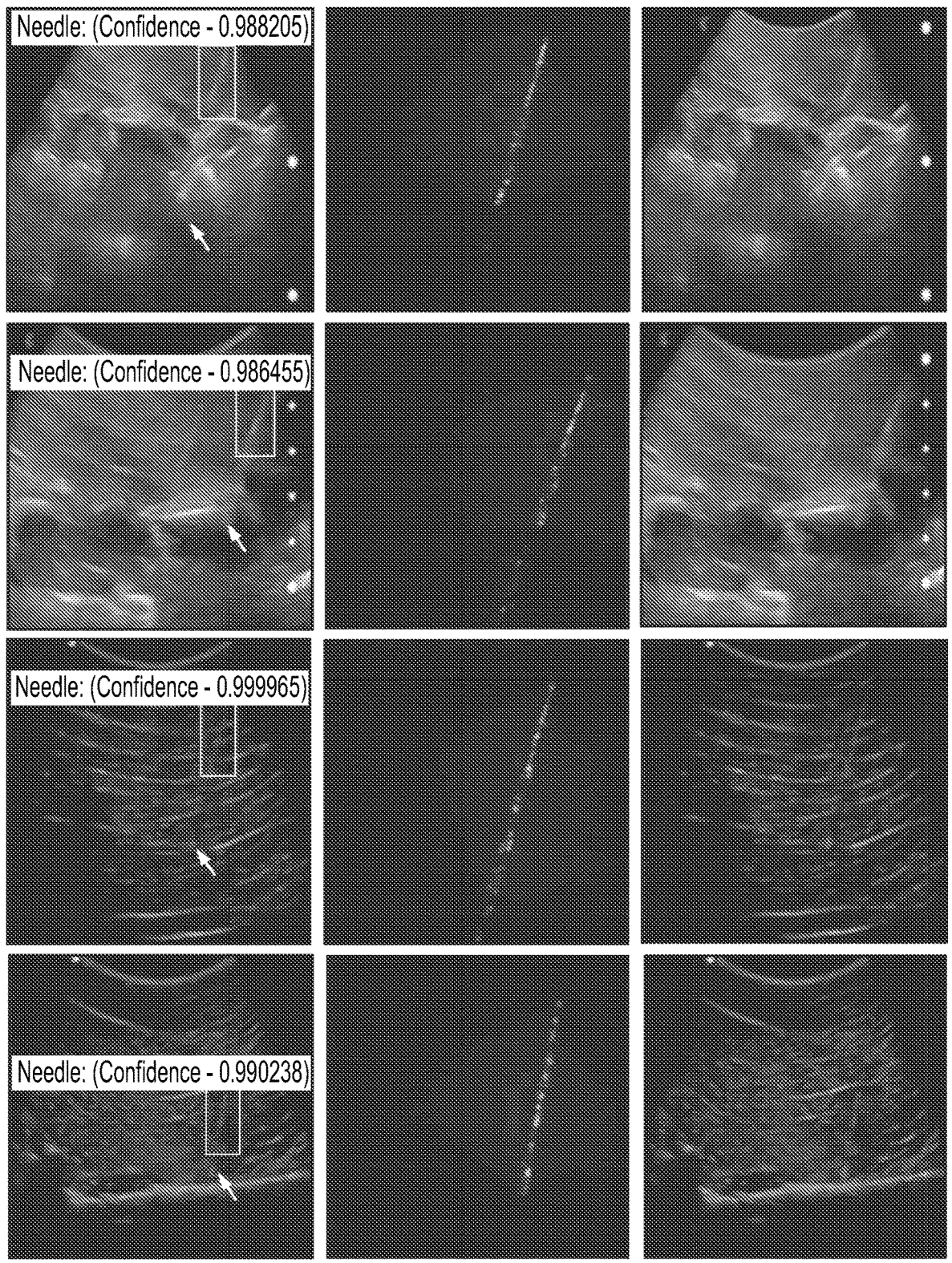

FIG. 13 is an illustration showing the needle tip localization process. Illustration 122 shows an ultrasound image. Illustration 124 shows an extended trajectory region computed with the Hough transform, which is used to form a trajectory mask. Illustration 126 shows an output of the MLESAC algorithm. Illustration 128 shows an enhanced needle image. Illustration 130 shows the localized tip 132. FIG. 14 is another illustration showing the needle tip localization process.

Figure 15:
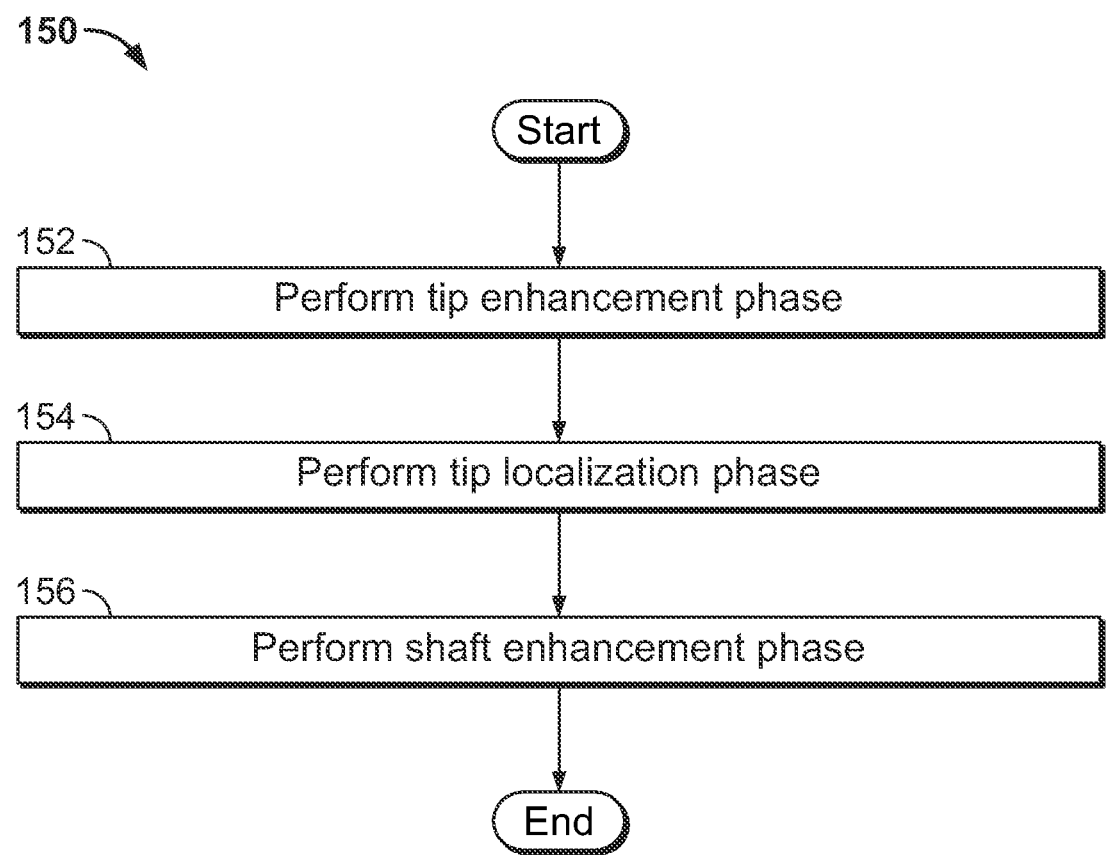
FIG. 15 is a flowchart illustrating overall process steps being carried out by a second embodiment of the system of the present disclosure.
Figure 16:
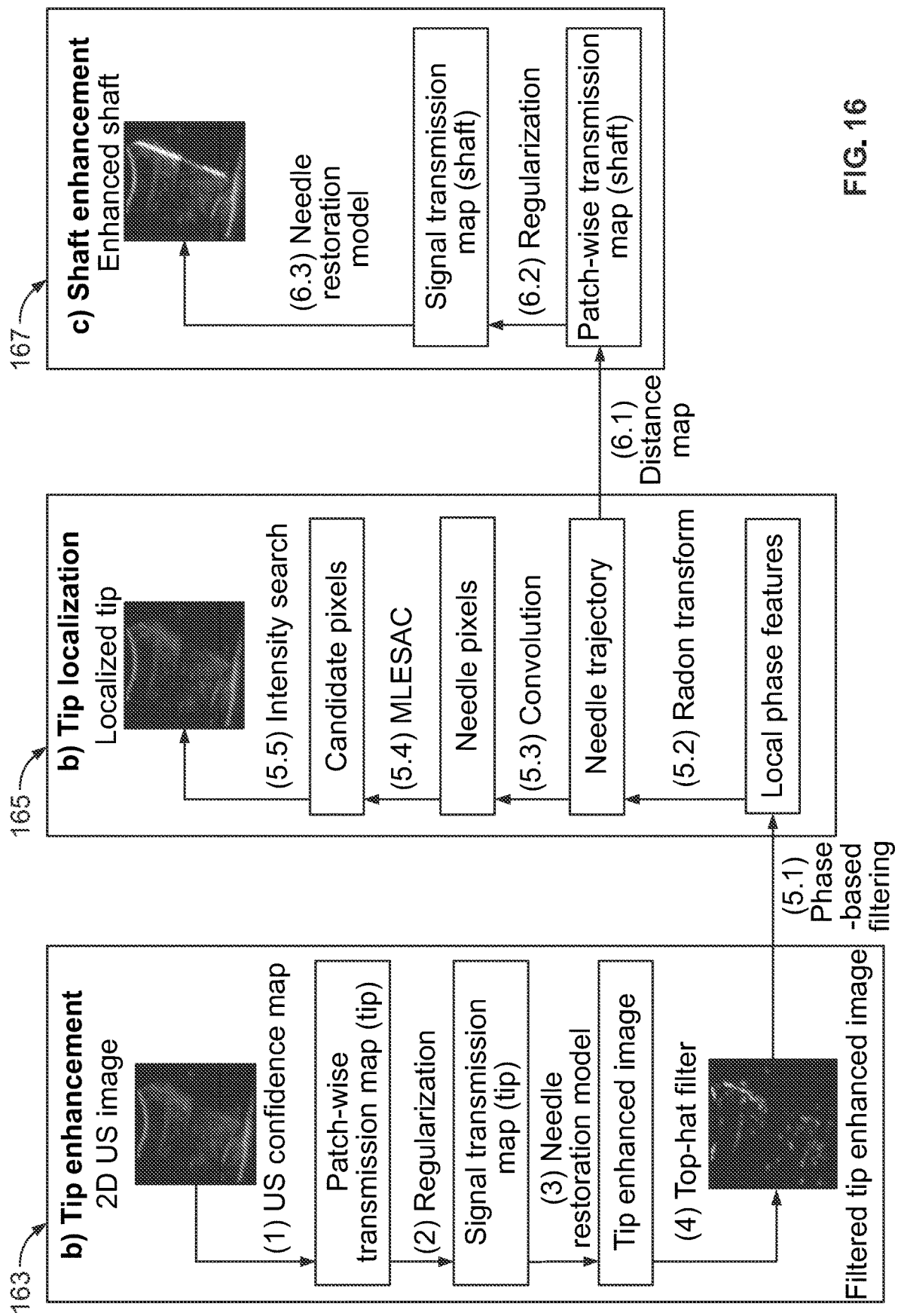

FIG. 15 shows a flowchart illustrating overall process steps being carried out by a second embodiment of the system, indicated generally at 150. Specifically, method 150 will enhance and localize a steeply inserted needle. In step 152, the system performs a tip enhancement phase. In step 154, the system performs a tip localization phase. In step 156, the system performs a shaft enhancement phase. Each phase will be discussed in greater detail below. FIGS. 16 and 17 are an illustration showing the tip enhancement phase, the tip localization phase and the shaft enhancement phase in more detail.

Figure 18:
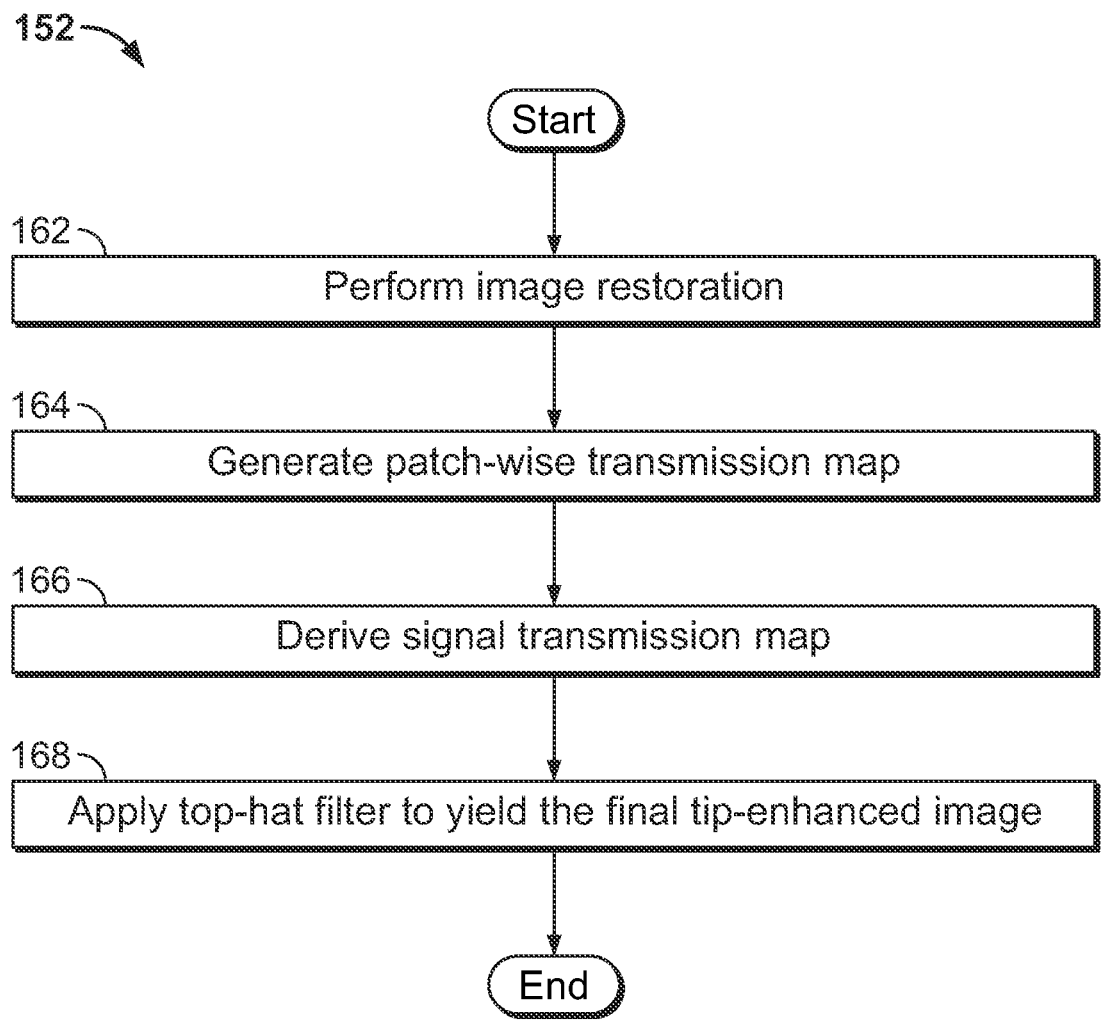
FIG. 18 is a flowchart illustrating step 152 of FIG. 15 in greater detail.

FIG. 18 shows a flowchart illustrating step 152 of FIG. 15 in greater detail. In particular, FIG. 18 illustrates process steps performed during the needle detection phase. In step 162, the system performs an image restoration. In an example, the system can account for attenuation and scattering by using a linear interpolation model. For example, the following formula can be used: I (x, y)=t (x, y) $I_e$ (x, y)+(1−t (x, y))v, where I (x, y) is an ultrasound image, t (x, y) is a depth-dependent signal transmission map function (representing response of a loss field in a transmission medium), $I_e$ (x, y) is an ultrasound image intensity to be recovered and v is a constant intensity equal to echogenicity of the tissue confining the needle. It should be noted that a bold notation denotes a matrix. An enhanced image is generated by the system using the following formula:

$$I_e(x, y) = \frac{I(x, y) - v}{[\max(t(x, y), \kappa)]^\alpha} + v$$

In the enhanced image formula, k=0.001, where k is a small constant that prevents division by zero.

In step 164, the system generates a patch-wise transmission map. In an example, the patch-wise transmission map is generated by the following formula: ψ (x, y)=$I_c$(x, y)*. $I_c$(x, y) denotes a confidence map, which results from a probability density function that assigns to each pixel in I(x, y) a probability that a random walk emanating from that pixel would be able to reach virtual transducer elements at the top of the ultrasound image, given ultrasound specific constraints, and * denotes a complement. The behavior of the confidence map is controlled by three free parameters, α, β, and γ. The free parameter α denote the attenuation coefficient which controls the depth-dependent attenuation rate. The free parameter β denotes an algorithm constant which affects the robustness and accuracy of segmentation. The free parameter γ models the beam width, imposing a penalty on random walks crossing a horizontal/diagonal edge in the graph with increasing corresponding distance from the starting scanline.

Figure 19:
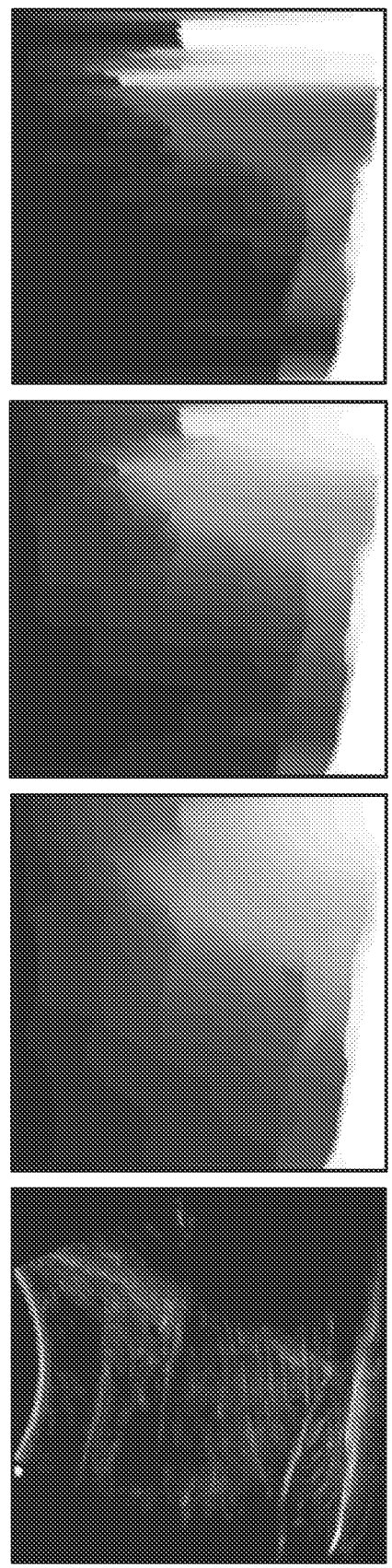
FIG. 19 is a set of images illustrating the effect of γ on the patch-wise transmission map.

FIG. 19 is an illustration showing the effect of γ on the patch-wise transmission map, ψ (x, y), while fixing α=2 and β=90. It should be noted that γ achieves a distinct function with minimum horizontal discontinuities.

In step 166 (FIG. 18), the system derives a signal transmission map. In an example, the signal transmission map, t(x,y), is derived by using the following formula:

$$\frac{\lambda}{2}\|t(x, y) - \psi(x, y)\|_2^2 + \sum_{i \in \Omega}\|W_i \circ (G_i * t(x, y))\|_1$$

Figure 20:
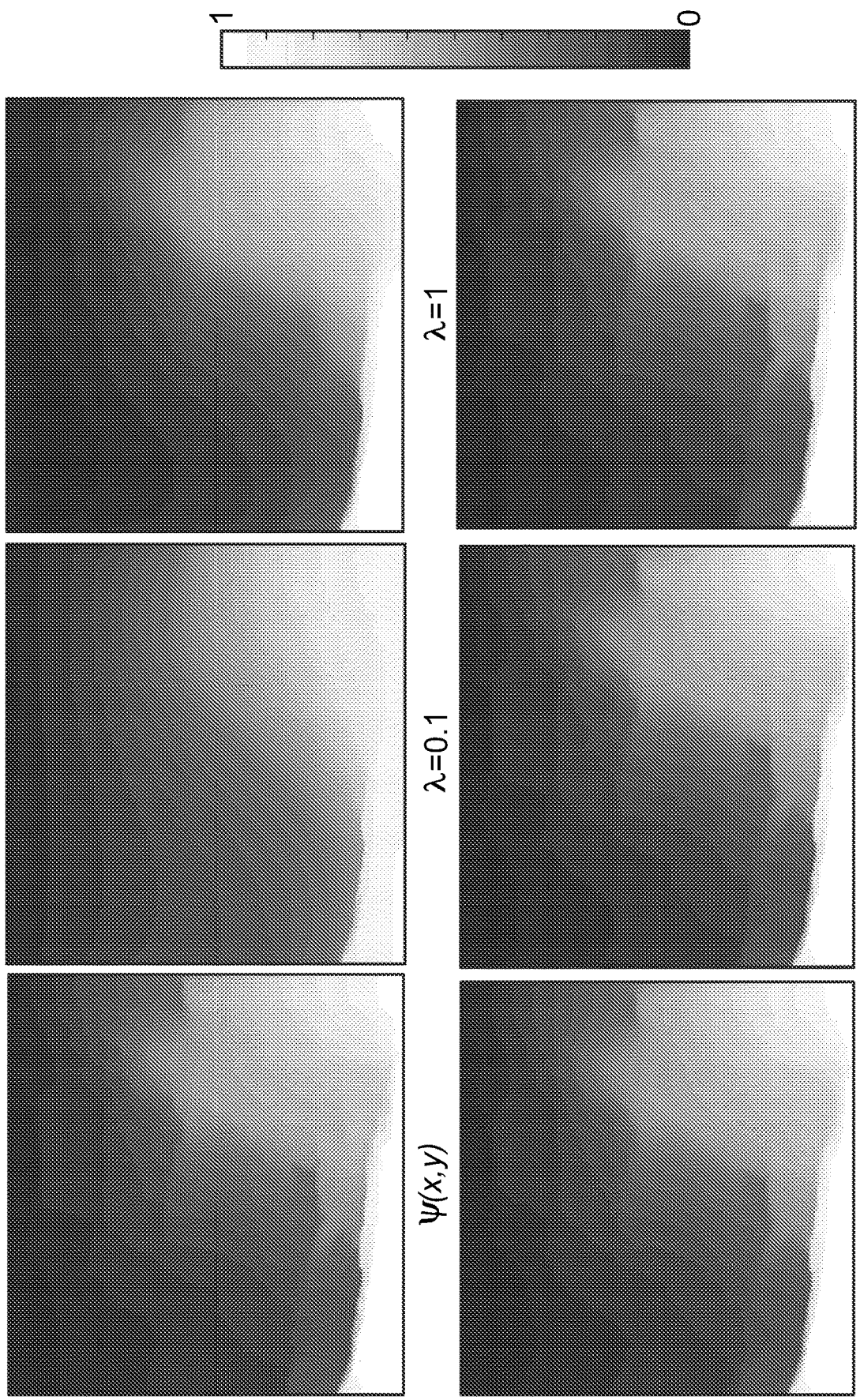
FIG. 20 is a set of images illustrating the derived signal transmission map.

The equation has two components. The first is the data which measures the closeness of t(x,y) to ψ (x, y), while the second introduces additional contextual constraints on t(x, y). A regulation parameter λ is used to balance the two parts. $G_i$ is a bank of high-order differential operators, consisting of 8 Kirsch filters. The 8 Kirsch filters consist of the same kernel mask rotated in 45-degree increments through all 8 compass directions. Combining the first-order derivative Kirsch filters with a second-order derivative Laplacian mask preserves edge features associated with the needle. W is a weighing function to further constrain t(x,y) in a local image patch. Considering two neighboring pixels, the weighing function is such that $W(t_2(x,y)-t_1(x,y))\approx 0$. If the two pixels are far apart, then W should be small, and vice versa. The system computes the weighing function from $W_i(q)=\exp(-|G_i*I(x,y))_Q|^2$, where Q is a given location in the image. When $t_2(x,y)=t_1(x,y)$, W=0. When W=0, the constraint on t(x,y) between neighboring pixels is eliminated. FIG. 20 is an illustration showing the result of deriving the signal transmission map t (x, y) from ψ (x, y) using various λ.

Figure 21:
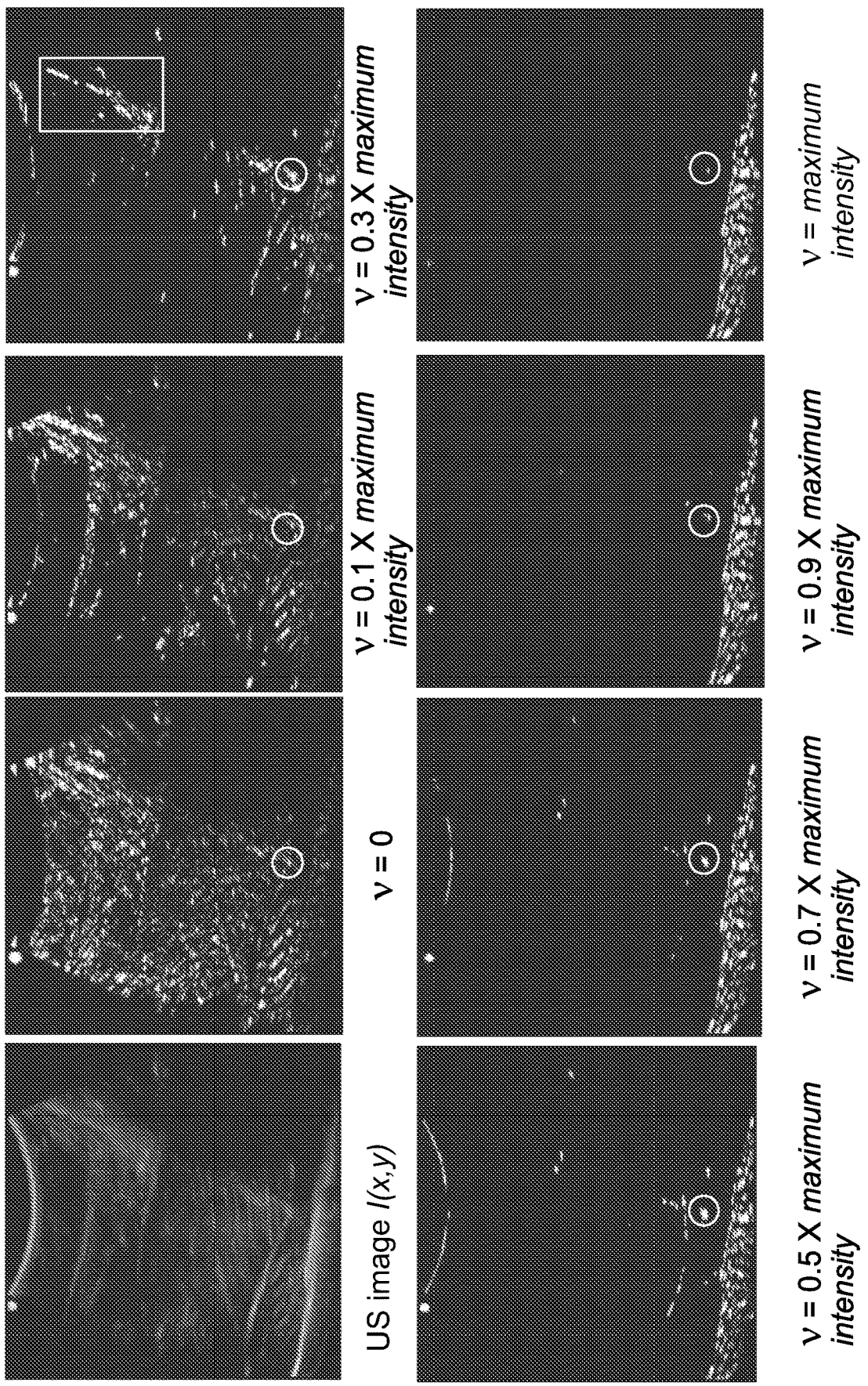
FIG. 21 is a set of images illustrating the output of the tip enhancement phase.

In step 168 (FIG. 18), the system applies a top-hat filter to yield a final tip-enhanced image. In an example, the top-hat filter (TF) computes the morphological opening of $I_e(x,y)$ and subtracts it from $I_e(x,y)$: $TF(I_e(x,y))=I_e(x,y)-D_L[E_L(I_e(x,y))]$, where L is a linear structuring element, $D_L$ denotes dilation operations, and $E_L$ denotes erosion operations. FIG. 21 is an illustration showing the output (e.g., the final tip-enhanced image) of the tip enhancement phase.

Figure 22:
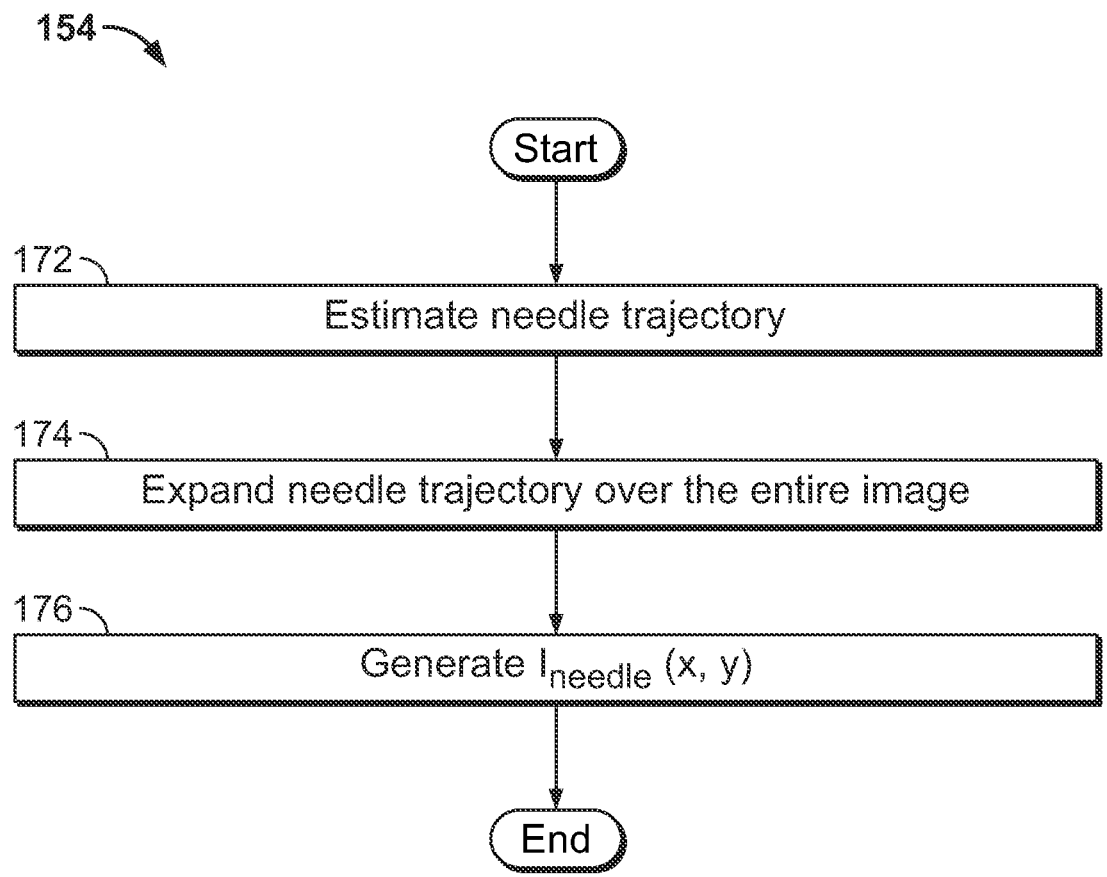
FIG. 22 is a flowchart illustrating step 154 of FIG. 15 in greater detail.
Figure 23:
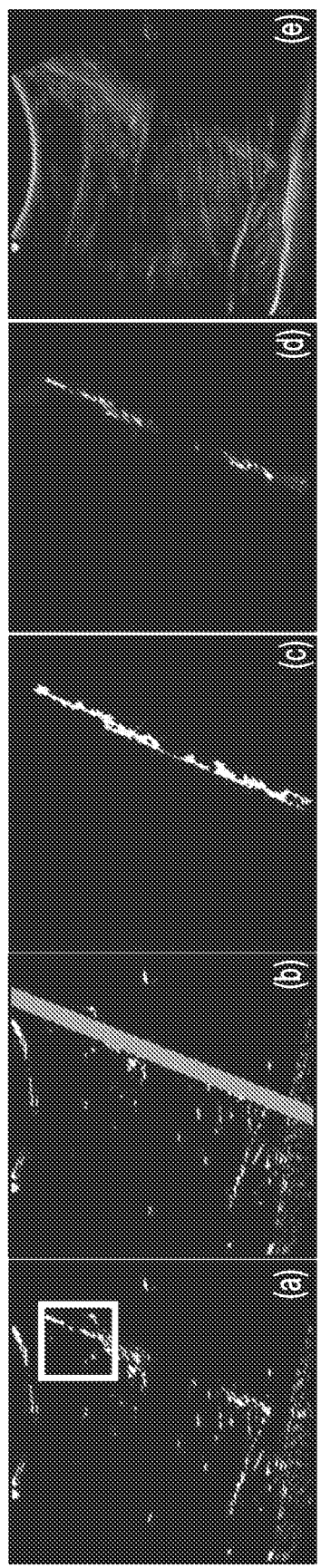
FIG. 23 is a set of images illustrating the automatic tip detection.

FIG. 22 shows a flowchart illustrating step 154 of FIG. 15 in greater detail. In particular, FIG. 22 illustrates process steps performed during the tip localization phase. In step 172, the system estimates the needle trajectory. In an example, the system estimates the needle trajectory by, first, extracting shaft information from the enhanced image $I_e$ $(x,y)_{tip}$. For example, for a 500×500 $I_e$ $(x,y)_{tip}$ enhanced image, a fixed 100×100 region of interest ($I_e$ ROI (x,y)), is defined on the intersection side of the needle. FIG. 23 is an illustration showing the automatic tip detection, where, in illustration (a), a fixed region of interest is defined. It should be noted that $I_e$ ROI (x,y) must contain part of the needle shaft, although it need not contain the needle tip. To extract the shaft information from $I_e$ ROI (x,y), the system uses a bank of orientation-tuned band-pass 2D Log-Gabor filters. The filters facilitate local phase-based processing, from which the resulting image descriptor is intensity invariant and therefore insensitive to ultrasound imaging variable such as tissue type. The resulting phase symmetry image PS (x, y), contains distinct local phase features for the needle shaft. The filter parameters are tuned to be optimal. Next, from the PS (x, y), the needle trajectory is estimated using the Radon transform with an angular range of 0°-179°.

In step 174 (FIG. 22), the system expands the needle trajectory over the entire $I_e$ $(x,y)_{tip}$ image, as can be seen in illustration (b) of FIG. 23. It should be noted that knowledge of the trajectory region can aid the system in extracting only data lying along the trajectory in $I_e$ $(x,y)_{tip}$ by convolution. The system then trims the data using a maximum likelihood estimation sample consensus (MLESAC) algorithm, which performs inlier detection and geometrical optimization. The resulting image ($I_{MLESAC}(x,y)$) is shown in illustration (c) of FIG. 23. Next, the system distributes the resulting collinear candidate intensities lying along a line L among a set of line segments, each defined by a set of points or knots denotes as $\mu_1 \ldots \mu_n$. The system then extracts the needle tip using the following formula:

$$I_{needle}(I_{BP}(x, y)) = \frac{\int_{\mu_i}^{\mu_{i+1}} I_{BP}(x, y) d\mu}{\|L_{(\mu_{i+1})} - L_{\mu_i}\|_2}; \mu \in [\mu_i, \mu_{i+1}]$$

The system obtains $I_{BP}$ (x, y) by applying a Log-Gabor filter without orientation selectivity to $I_e$ $(x, y)_{tip}$, where $\mu_1$ and $\mu_{i+1}$ are successive knots. The system, using the above needle tip formula, assigns to pixels between knots $\mu_1$ and $\mu_{i+1}$, a mean intensity value along L. In step 176, the system generates $I_{needle}$ (x, y), which can be seen in illustration (d) of FIG. 23. The system then, from $I_{needle}$ (x, y), localizes the needle tip as the farthest maximum intensity pixel at the distal end of the needle trajectory, which is illustrated in illustration (e) of FIG. 23.

Figure 24:
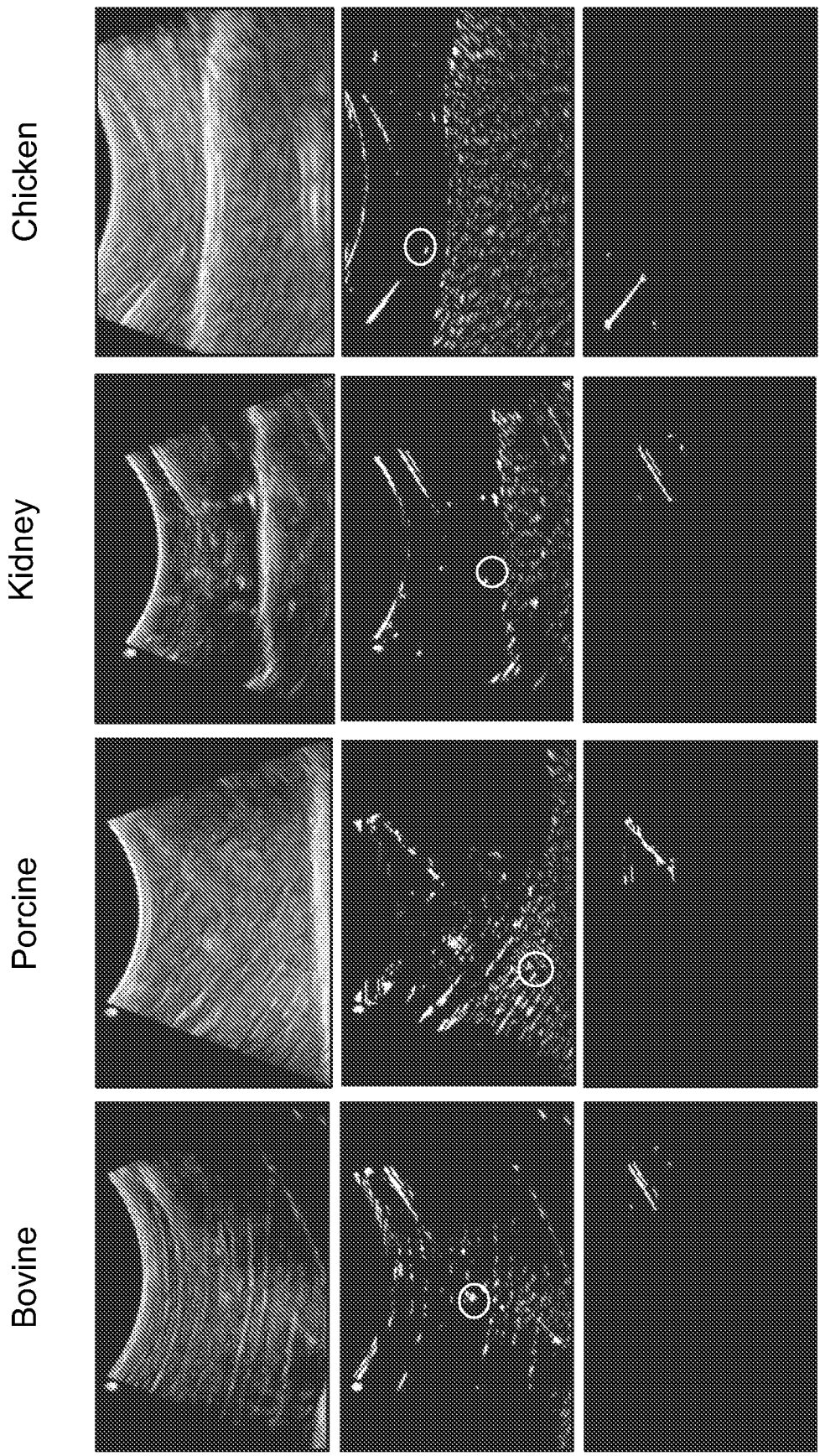
FIG. 24 is a set of images illustrating tissue independence of a PS(x,y) image for four different tissue types.

FIG. 24 is an illustration showing tissue independence of PS (x, y) image for four different tissue types: bovine, porcine, kidney and chicken. The top row shows an ultrasound image I (x, y). The middle row shows a tip enhanced image $I_e$ (x, y)$_{tip}$. The enhanced tip is surrounded by the circle. The bottom row shows the PS (x, y) image.

Figure 25:
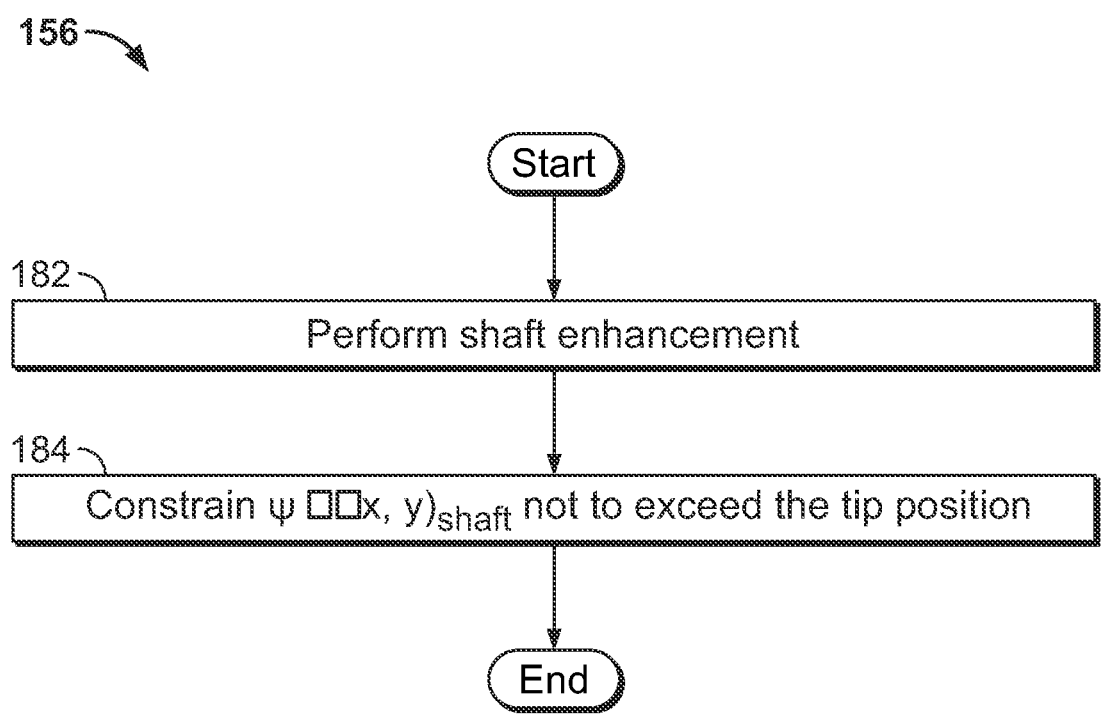
FIG. 25 is a flowchart illustrating step 156 of FIG. 15 in greater detail.

FIG. 25 shows a flowchart illustrating step 156 of FIG. 15 in greater detail. In particular, FIG. 25 illustrates process steps performed during the shaft enhancement phase. In step 182, the system performs a shaft enhancement using the following formula:

$$\psi(x, y)_{shaft} = \frac{|\sigma(x, y) - \max(\sigma(x, y))|}{\max(\sigma(x, y))}$$

Figure 26:
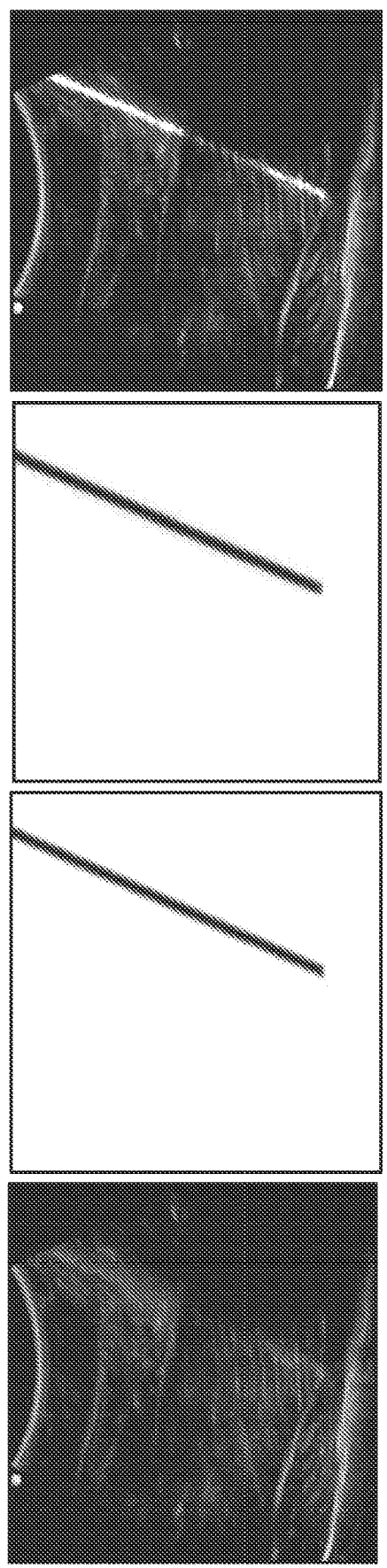
FIG. 26 is a set of images illustrating the needle shaft enhancement process.
Figure 27:
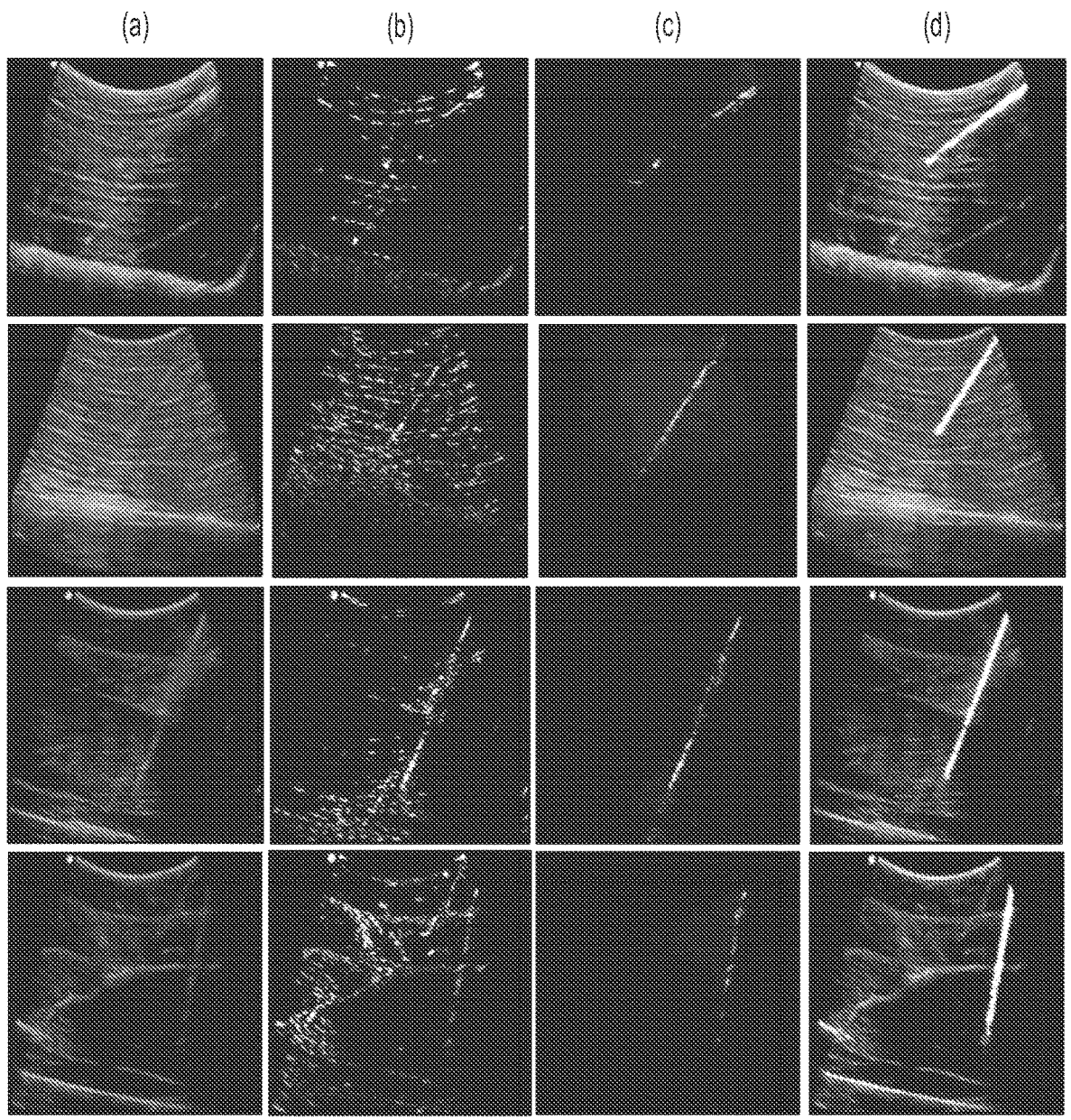
FIG. 27 is a set of images illustrating the shaft enhancement and tip localization at steep insertion angles.

In step 184, the system constrains ψ (x, y)$_{shaft}$ not to exceed the tip position. The system obtains the signal transmission map for the shaft, t(x,y)$_{shaft}$, from the signal transmission map formula and shaft restoration is performed using enhanced image formula, where v=max(I(x,y)). FIG. 26 is an illustration showing the needle shaft enhancement process. It should be noted that t(x,y)$_{shaft}$ has low intensities along the needle axis and higher intensities for image regions away from the axis. The enhanced shaft arises from a local average of pixels belongings to the shaft along the trajectory. FIG. 27 is an illustration showing shaft enhancement and tip localization at steep insertion angles.

Figure 28:
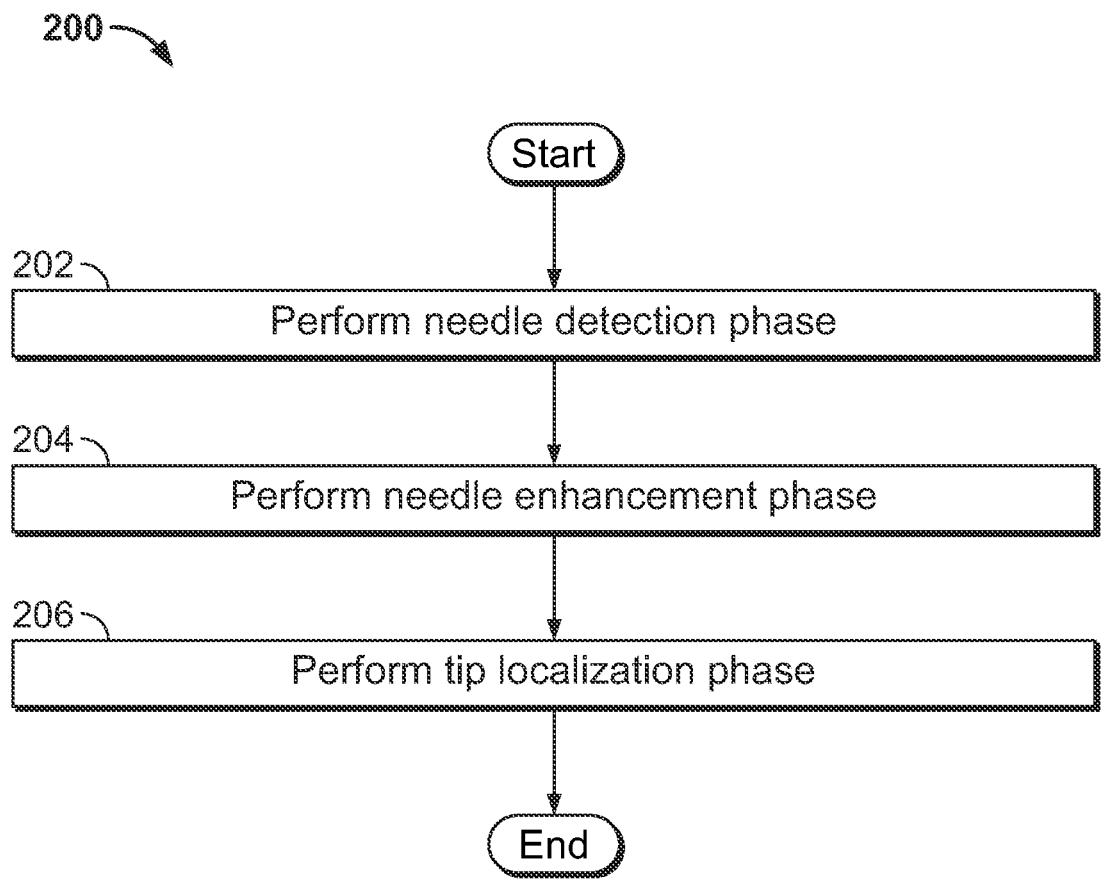
FIG. 28 is a flowchart illustrating overall process steps being carried out by a third embodiment of the system of the present disclosure.
Figure 29:
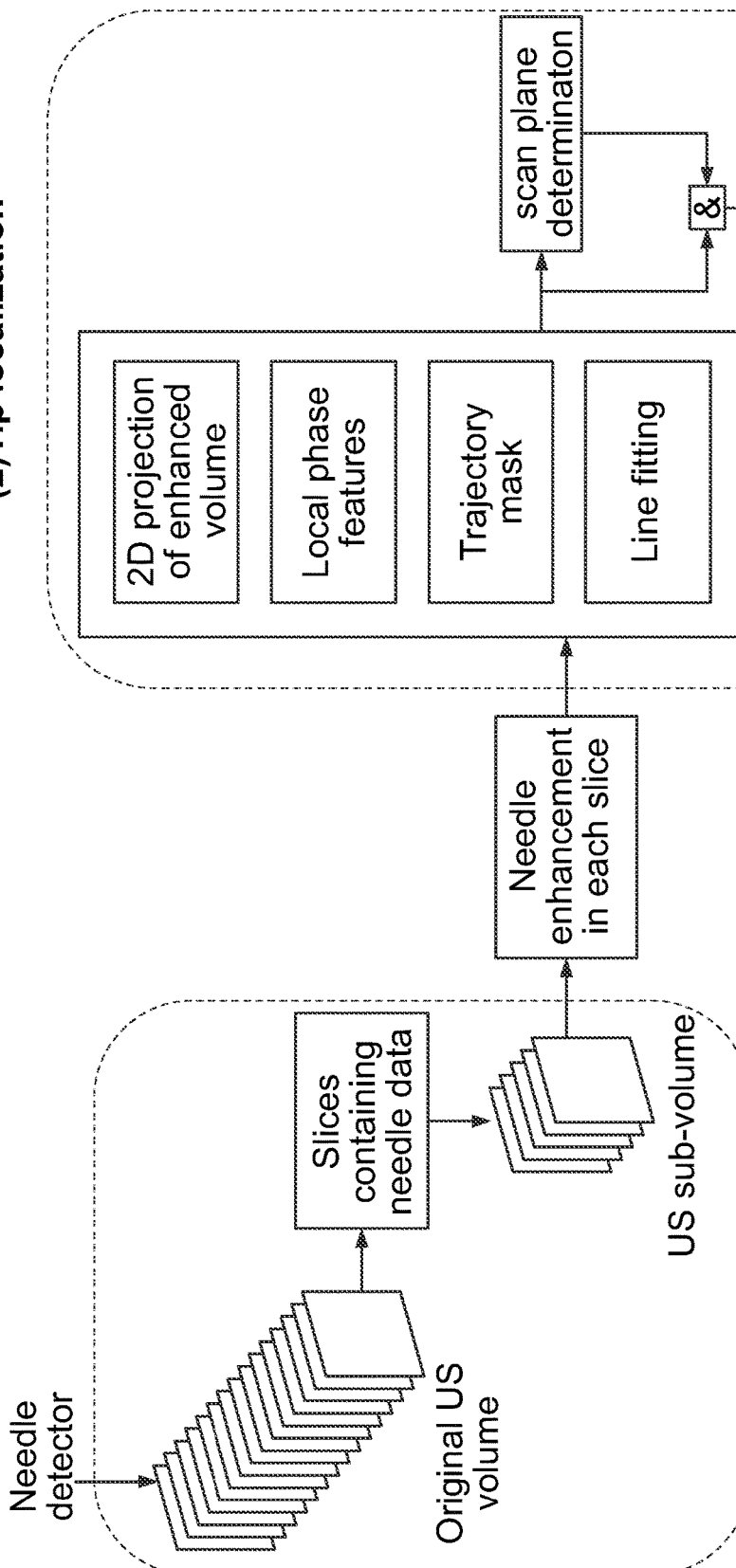
FIG. 29 is a diagram illustrating the phases of the method 200.

FIG. 28 shows a flowchart illustrating overall process steps being carried out by a third embodiment of the system, indicated generally at 200. Specifically, method 200 will automatically detect and enhance needles under 3D ultrasound guidance. In step 202, the system performs a needle detection phase. In step 204, the system performs a needle enhancement phase. In step 206, the system performs a tip localization phase. FIG. 29 is an illustration showing the phases of method 200.

Figure 30:
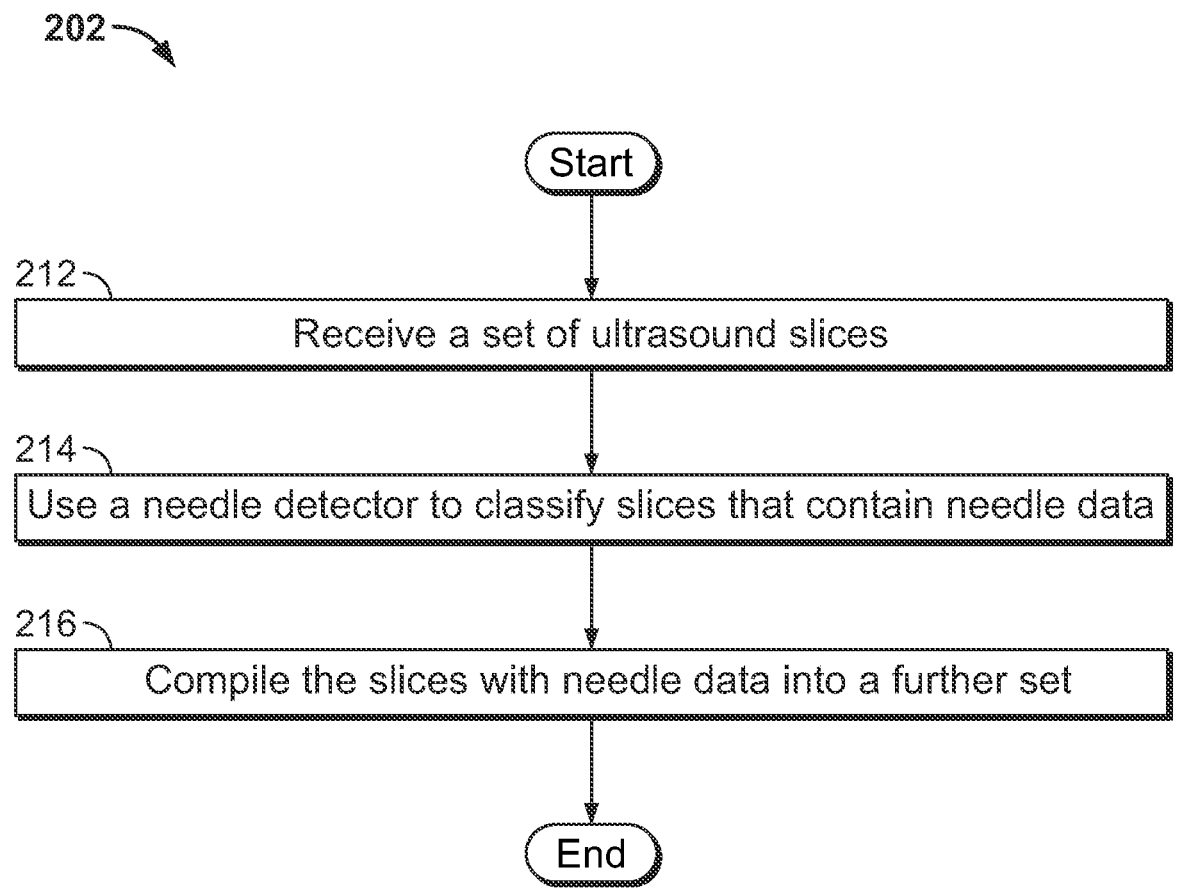
FIG. 30 is a flowchart illustrating step 202 of FIG. 28 in greater detail.
Figure 31:
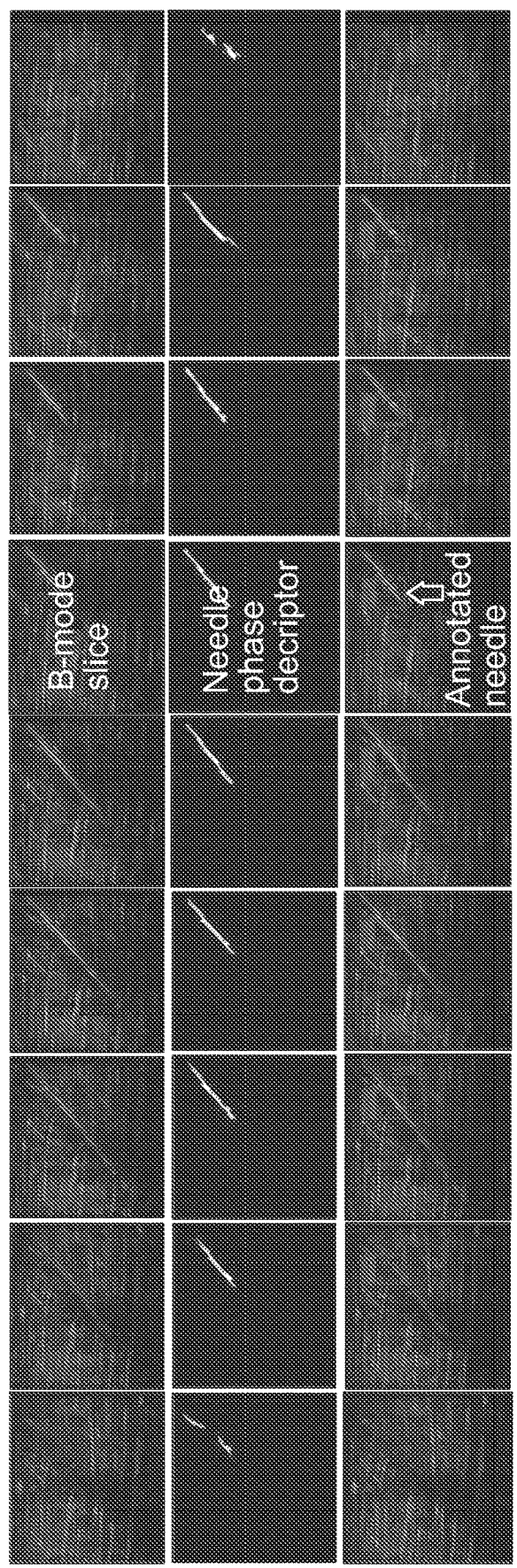
FIG. 31 is a set of images illustrating the needle phase detection phase.

FIG. 30 shows a flowchart illustrating step 202 of FIG. 28 in greater detail. In particular, FIG. 30 illustrates process steps performed during the needle detection phase. In step 212, the system receives a set of ultrasound slices. In step 214, the system uses a needle detector to classify slices that contain needle data. In an example, the system applies orientation tuned intensity invariant local phase filter banks to each ultrasound slice in the set (hereafter denoted as US$_{volume}$) to extract a needle phase descriptor, hereafter denoted as NPD(x,y). The filter banks are constructed from 2D Log-Gabor filters, whose parameters are selected automatically. It should be noted that the insertion side of the needle is known a priori, and the calculation is limited to an automatically selected region of interest. On the insertion side it is expected that the ROI contains a visible part of the shaft. The output of the filter operation generates a phase-based descriptor called phase symmetry, PS(x,y), which is used as an input to the MLESAC algorithm. The system can use the MLESAC algorithm to prune false positive pixels and connect inliers to yield NPD(x,y). FIG. 31 is an illustration showing the needle detection phase and examples of slices with and without NPD(x,y). The top row shows B-mode US slices constituent of $US_{volume}$. The middle row shows respective NPD(x,y) images. The slices with needle data possess a salient straight feature with minimum bending. The slices without needle data lack such features. The bottom row shows slice classification results.

The needle detector uses an $L_2$-Hys (Lowe-style clipped $L_2$-norm) contrast normalization on overlapping 33 cells blocks of 4×4 pixel cells. The detector is applied to each of the slices in the $US_{volume}$ after preprocessing to elicit needle phase descriptors similar to those used in training the needle detector. In step 216, the system compiles the slices with needle data into a further set. The further set consists of only slices that contain needle data.

Figure 32:
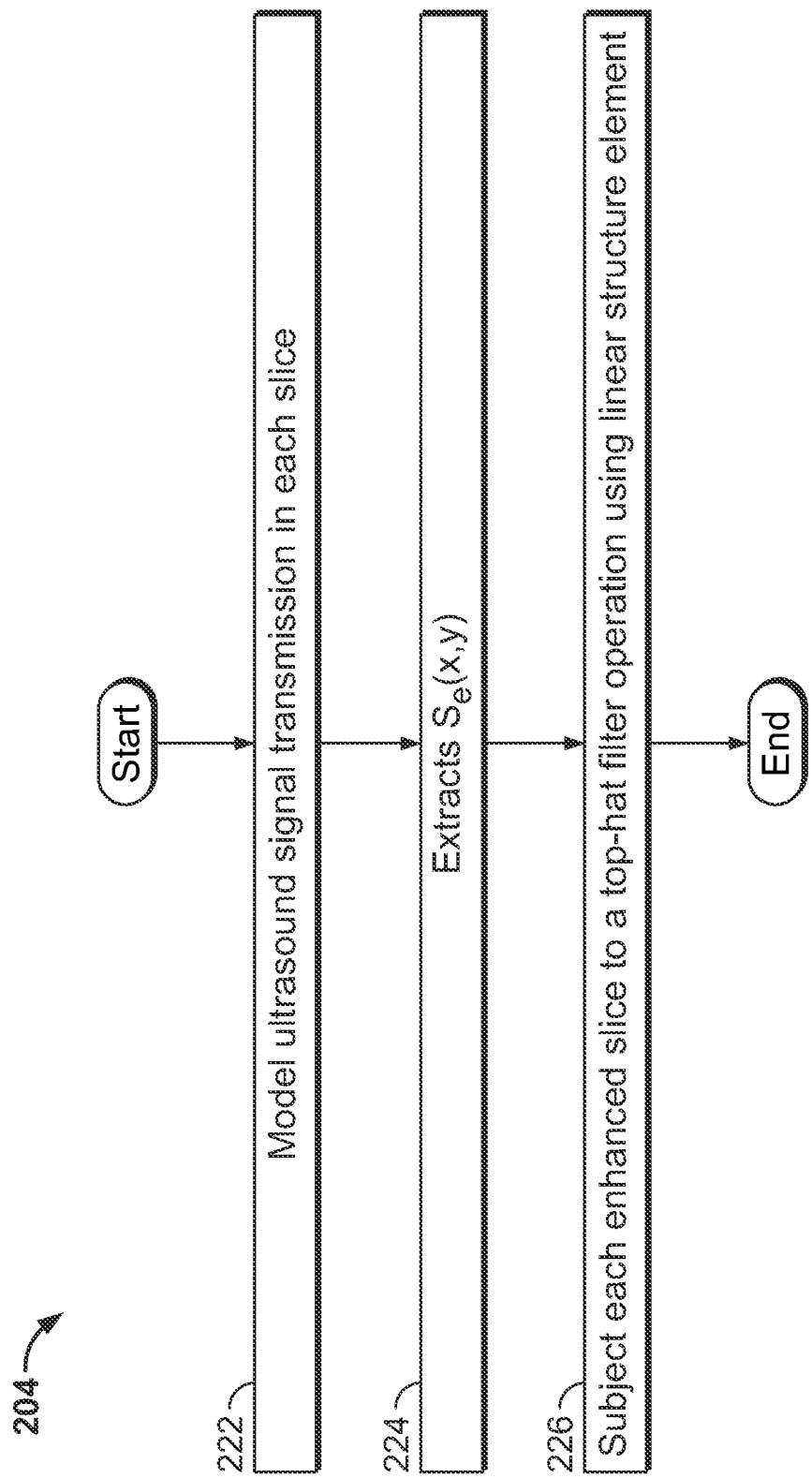
FIG. 32 is a flowchart illustrating step 204 of FIG. 28 in greater detail.

FIG. 32 shows a flowchart illustrating step 204 of FIG. 28 in greater detail. In particular, FIG. 32 illustrates process steps performed during the needle enhancement phase. In step 222, the system models ultrasound signal transmission in each slice. In an example, each slice is modeled as $S(x,y)=S_t(x,y)S_e(x,y)+(1-S_t(x,y))k$. $S(x,y)$ is a slice in the $US_{volume}$, $S_e(x,y)$ is the signal transmission map, $S_e(x,y)$ is the desired enhanced image, and k is the average intensity of the tissue surrounding the needle in attenuated regions. $S_t(x,y)$ is obtained by minimizing the following objection function:

$$\frac{\lambda}{2}\|S_t(x, y) - S_a(x, y)\|_2^2 + \sum_{i \in \zeta} \|\Gamma_i \circ (R_i \star S_t(x, y))\|_1$$

$S_a(x,y)$ is a patch-wise transmission function representing boundary constraints imposed on the image by attenuation and orientation of the needle, $\zeta$ is an index set of image pixels, ∘ is element wise multiplication, and ★ is a convolution operator. $R_i$ is a bank of high order differential filters consisting of eight Kirsch filters and one Laplacian filter, and $\Gamma_i$ is a weighing matrix calculated from $\Gamma_i$ (x,y) $=\exp(-|R_i(x,y) \star S(x,y)|^2)$.

In step 224, the system extracts $S_e(x,y)$. In an example, the system extracts $S_e(x,y)$ from $S_e(x,y)=[(S(x,y)-k)/[\max(S_t(x,y),\varepsilon)]^\rho]+k$. $\varepsilon$ is a small constant and $\rho$ is related to the attenuation co-efficient of the tissue. In step 226, the system subjects each enhanced slice to a Top-hat filter operation using a linear structure element. The final enhanced slices constitute the enhanced sub-volume denoted as $USE^*_{volume}$.

Figure 33:
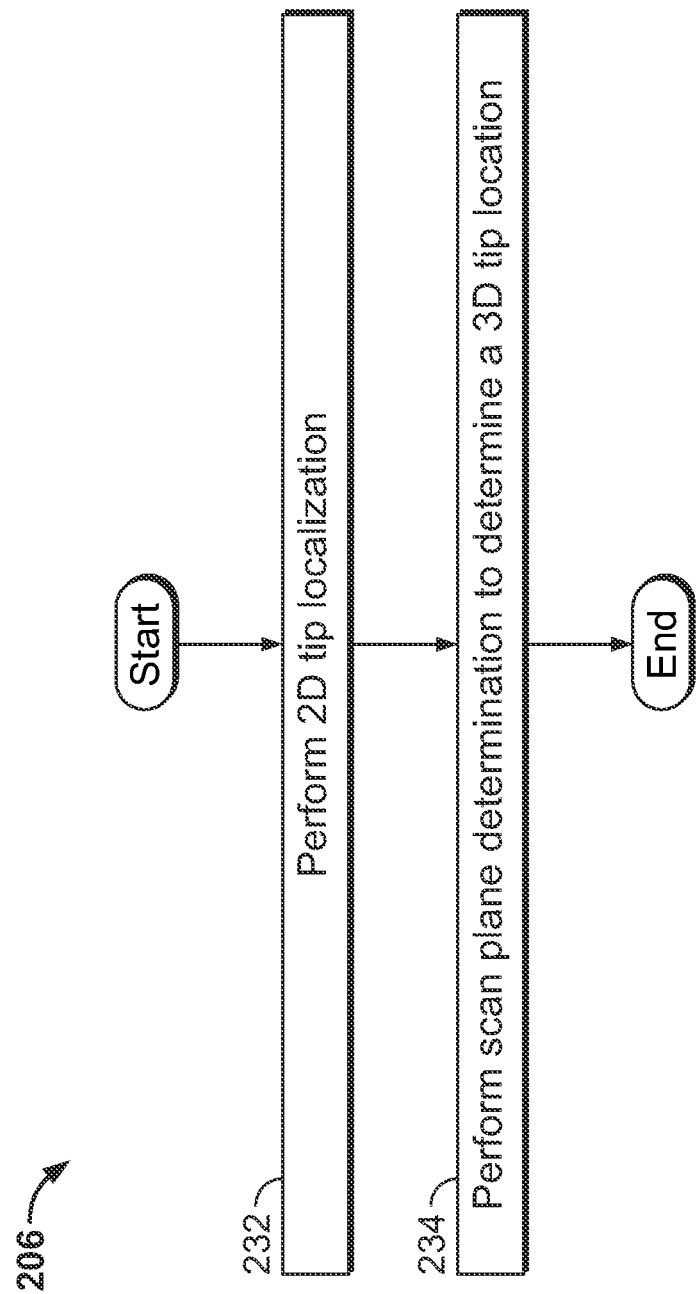
FIG. 33 is a flowchart illustrating step 206 of FIG. 28 in greater detail.

FIG. 33 shows a flowchart illustrating step 206 of FIG. 28 in greater detail. In particular, FIG. 33 illustrates process steps performed during the tip localization phase. In step 232, the system performs a 2D tip localization. In an example, when the needle insertion is in the y-z plane, then the x-y plane is parallel to the needle insertion direction. The system determines x' and y' from a projection $P_{x,y}$ since x' and y' have the same value in all slices. $P_{x,y}$ is calculated as the maximum intensity projection (MIP) of $USE^*_{volume}$, by extracting maximum intensity values along optical paths in the z direction. From the projection, the needle tip is localized by determining the phase symmetry PS(x,y) of $P_{x,y}$ in a region limited to the needle trajectory, applying the MLESAC algorithm for inlier detection and geometrical optimization, and feature extraction on the resultant point cloud using a combination of spatially distributed image statistics which enhance the needle tip. The system then yields the projection enhanced needle image denoted as PE(x,y). (x',y') is determined from the first maximum intensity pixel at the distal end of the needle trajectory in PE(x,y).

In step 234, the system performs a scan plane determination to determine a 3D tip location. In an example, the system determines the scan plane by calculating elevation (z) direction of the volume. The system can calculate the scan plane by using the following formula:

$$\sum_{i=-\gamma}^{+\gamma} \sum_{j=-\gamma}^{+\gamma} I(x' + i, y' + j)$$

Figure 34:
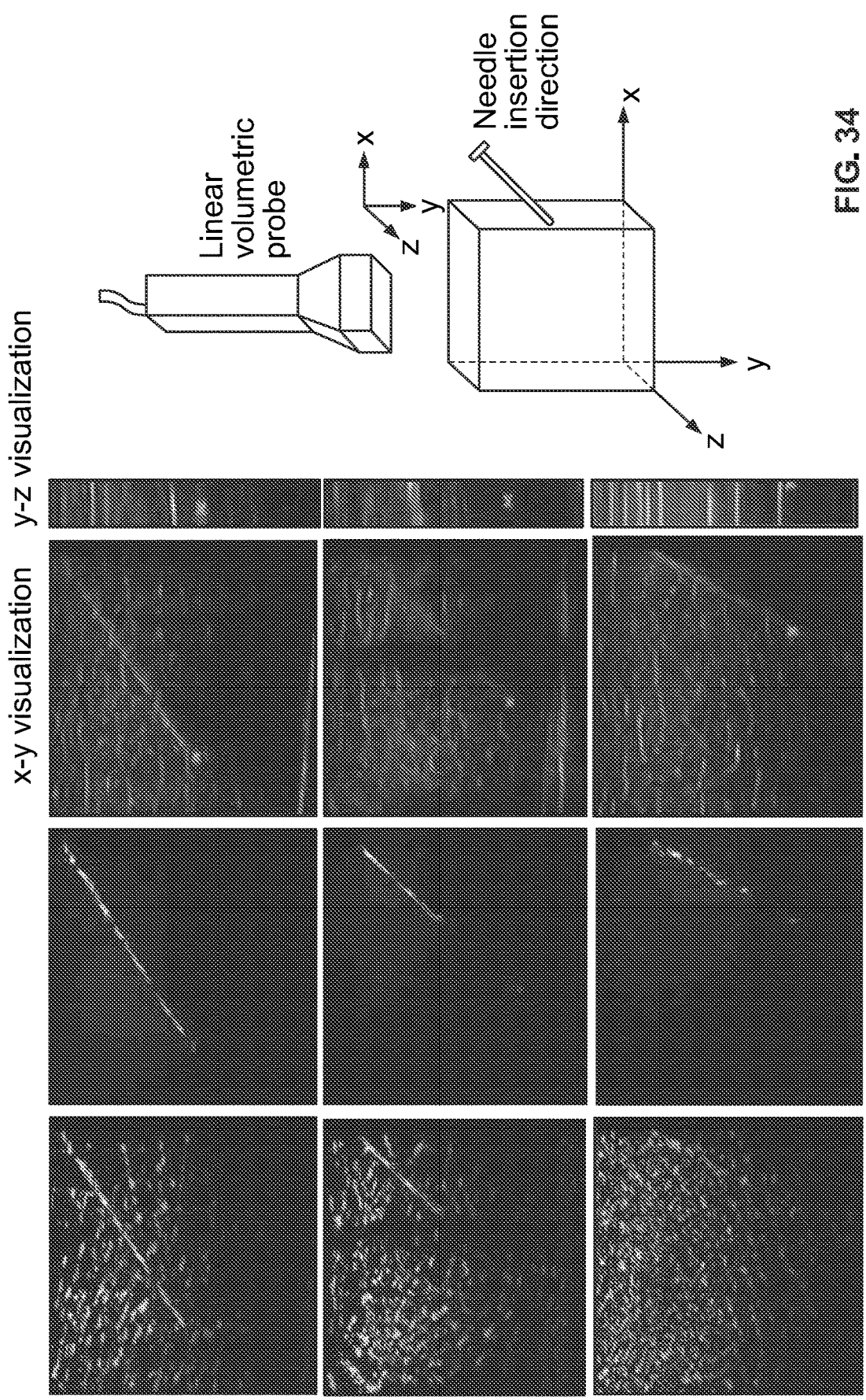
FIG. 34 is a set of images illustrating the tip localization phase.

The sum of pixel intensities in a bounded square patch of length $2\gamma$ centered at (x',y') in each slice within $USE^*_{volume}$. The system estimates the scan plane as the slice with the maximum intensity sum. The result produces z'. FIG. 34 is an illustration showing the tip localization phase. The first column shown a $P_{x,y}$ image. The second column shows a PE(x,y) image. The automatically localized tip is overlaid on x-y in the third column, and on y-z in the fourth column. The fifth column shows 3D imaging coordinates. The top row shows a moderate insertion angle and the needle aligned with the ultrasound beam. The middle row shows a moderate insertion angle and the needle not aligned with the ultrasound beam. The bottom row shows a steep insertion angle and the needle aligned with the ultrasound beam.

Figure 35:
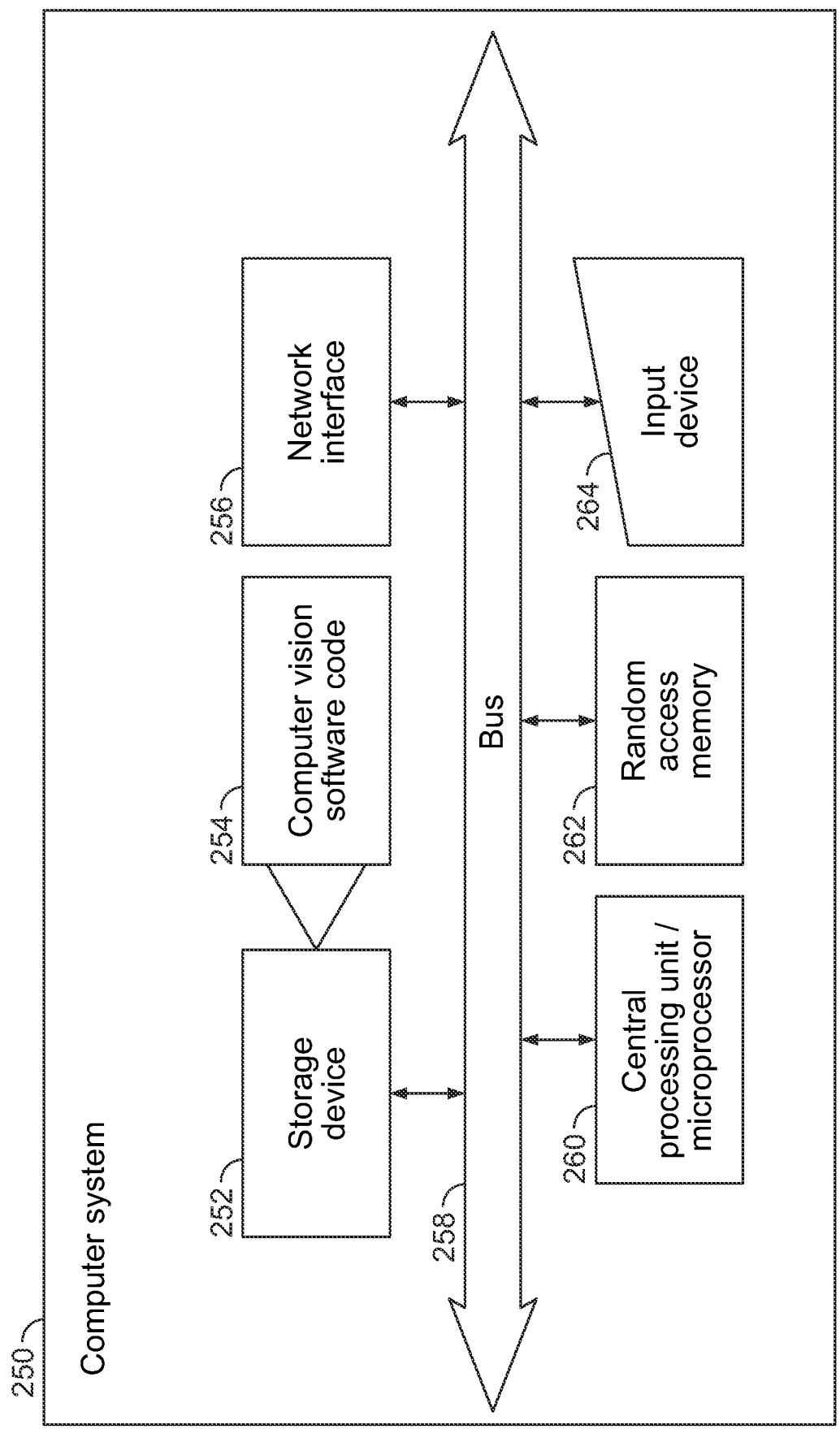
FIG. 35 is a diagram illustrating hardware and software component capable of implementing the system of the present disclosure.

FIG. 35 is a diagram showing a hardware and software components of a computer system 250 on which the system of the present disclosure can be implemented. The computer system 250 can include a storage device 252, computer vision software code 254, a network interface 256, a communications bus 258, a central processing unit (CPU) (microprocessor) 260, a random access memory (RAM) 264, and one or more input devices 266, such as a keyboard, mouse, etc. The computer system 250 could also include a display (e.g., liquid crystal display (LCD), cathode ray tube (CRT), etc.). The storage device 252 could comprise any suitable, computer-readable storage medium such as disk, non-volatile memory (e.g., read-only memory (ROM), eraseable programmable ROM (EPROM), electrically-eraseable programmable ROM (EEPROM), flash memory, field-programmable gate array (FPGA), etc.). The computer system 802 could be a networked computer system, a personal computer, a server, a smart phone, tablet computer etc. It is noted that the computer system 250 need not be a networked server, and indeed, could be a stand-alone computer system.

Having thus described the system and method in detail, it is to be understood that the foregoing description is not intended to limit the spirit or scope thereof. It will be understood that the embodiments of the present disclosure described herein are merely exemplary and that a person skilled in the art can make any variations and modification without departing from the spirit and scope of the disclosure. All such variations and modifications, including those discussed above, are intended to be included within the scope of the disclosure. What is intended to be protected by Letters Patent is set forth in the following claims.

What is claimed is:

1. A method for detecting placement of a medical device in an ultrasound image, comprising:
   receiving an ultrasound image;
   processing the image to generate one or more candidate regions within the image using a first neural network, each of the one or more candidate regions being a portion of the image and including a coarse localization of the medical device within the region;

selecting a proposed region from the one or more candidate regions using the first neural network;

assigning a score to the proposed region using the first neural network; and processing the proposed region selected from the one or more candidate regions and generated by the first neural network using a second neural network to further localize and classify the medical device in the proposed region, wherein the step of processing the image to generate the one or more candidate regions includes processing a feature map using a sliding convolution window to generate a plurality of anchor boxes and processing the plurality of anchor boxes to generate the one or more candidate regions.

2. The method of claim 1, wherein the score is related to an overlap with ground-truth object information in the ultrasound image.

3. The method of claim 1, wherein the medical device is a needle.

4. The method of claim 1, wherein the first neural network is a regional proposal network ("RPN").

5. The method of claim 4, wherein RPN is modeled as a fully convolutional network ("FCN").

6. The method of claim 1, wherein the second neural network is a fast region-based convolutional neural network ("R-CNN").

7. The method of claim 6, wherein the R-CNN comprises of three convolution layers and two fully connected layers.

8. The method of claim 1, wherein generating one or more candidate regions comprises ranking potential bounding boxes for the medical device.

9. The method of claim 8, further comprising:
reducing a number of potential bounding boxes by cross-boundary elimination.

10. The method of claim 1, further comprising estimating a trajectory of the medical device in the image.

11. The method of claim 10, wherein the step of estimating the trajectory comprises determining an insertion side and an insertion angle of the medical device, eliminating artifacts not belonging to the medical device, and applying a Hough transform to the image to determine the trajectory of the medical device.

12. A system for detecting placement of a medical device in an ultrasound image, comprising:
a computer system comprising a first neural network and a second neural network, wherein the computer system:
receives an ultrasound image;
processes the digital image to generate one or more candidate regions within the digital image using the first neural network, each of the one or more candidate regions being a portion of the image and including a coarse localization of the medical device within the region;
selects a proposed region from the one or more candidate regions using the first neural network;
assigns a score to the proposed region using the first neural network; and
processes the proposed region selected from the one or more candidate regions and generated by the first neural network using the second neural network to further localize and classify the medical device in the proposed region,
wherein the image is processed by applying a sliding convolution window to a feature map to generate a plurality of anchor boxes, and the plurality of anchor boxes are processed to generate the one or more candidate regions.

13. The system of claim 12, wherein the score is related to an overlap with ground-truth object information in the ultrasound image.

14. The system of claim 12, wherein the medical device is a needle.

15. The system of claim 12, wherein the first neural network is a regional proposal network ("RPN").

16. The system of claim 15, wherein RPN is modeled as a fully convolutional network ("FCN").

17. The system of claim 12, wherein the second neural network is a fast region-based convolutional neural network ("R-CNN").

18. The system of claim 17, wherein the R-CNN comprises of three convolution layers and two fully connected layers.

19. The system of claim 12, wherein the first neural network generates the one or more candidate regions by ranking potential bounding boxes for the medical device.

20. The system of claim 19, wherein the system reduces a number of potential bounding boxes by cross-boundary elimination.

21. The system of claim 12, wherein the computer system estimates a trajectory of the medical device in the image.

22. The system of claim 21, wherein the computer system determines an insertion side and an insertion angle of the medical device, eliminates artifacts not belonging to the medical device, and applies a Hough transform to the image to determine the trajectory of the medical device.

* * * * *

UNITED STATES PATENT AND TRADEMARK OFFICE
CERTIFICATE OF CORRECTION

PATENT NO. : 11,638,569 B2
APPLICATION NO. : 16/436284
DATED : May 2, 2023
INVENTOR(S) : Mwikirize et al.

It is certified that error appears in the above-identified patent and that said Letters Patent is hereby corrected as shown below:

On the Title Page

On page 3, under References Cited Other Publications Column 2, Line 51:
"Jhercik, et al." should be deleted and replaced with "Uhercik, et al."

Signed and Sealed this
Twenty-ninth Day of August, 2023

Katherine Kelly Vidal
*Director of the United States Patent and Trademark Office*